(12) United States Patent
Nakajima

(10) Patent No.: US 10,105,106 B2
(45) Date of Patent: Oct. 23, 2018

(54) EXERCISE INFORMATION DISPLAY SYSTEM, EXERCISE INFORMATION DISPLAY METHOD AND COMPUTER-READABLE RECORDING MEDIUM

(71) Applicant: CASIO COMPUTER CO., LTD., Shibuya-ku, Tokyo (JP)

(72) Inventor: Mitsuyasu Nakajima, Mizuho-machi (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 374 days.

(21) Appl. No.: 14/942,803

(22) Filed: Nov. 16, 2015

(65) Prior Publication Data

US 2016/0166880 A1    Jun. 16, 2016

(30) Foreign Application Priority Data

Dec. 12, 2014 (JP) ................................ 2014-251931

(51) Int. Cl.
*A61B 5/00* (2006.01)
*G06F 19/00* (2018.01)
(Continued)

(52) U.S. Cl.
CPC ............ *A61B 5/743* (2013.01); *A61B 5/1121* (2013.01); *A61B 5/486* (2013.01); *A61B 5/6829* (2013.01);
(Continued)

(58) Field of Classification Search
None
See application file for complete search history.

(56) References Cited

U.S. PATENT DOCUMENTS

| 5,524,637 | A | * | 6/1996 | Erickson | .............. A61B 5/1038 482/8 |
| 5,955,667 | A | | 9/1999 | Fyfe | |
| 5,963,891 | A | * | 10/1999 | Walker | .................... G06F 3/011 345/959 |

(Continued)

FOREIGN PATENT DOCUMENTS

| CN | 103759739 A | 4/2014 |
| JP | 2012000343 A | 1/2012 |

(Continued)

OTHER PUBLICATIONS

Chinese Office Action dated Sep. 1, 2017 issued in counterpart Chinese Application No. 201510920646.6.

(Continued)

*Primary Examiner* — Bruk Gebremichael
(74) *Attorney, Agent, or Firm* — Holtz, Holtz & Volek PC

(57) ABSTRACT

Provided is an exercise information display system including a sensor unit attached to an ankle of one leg of a human body to output data on a motion state of the leg and a control unit processing the data. The control unit acquires a parameter based on data output from the sensor unit in a case where the human body performs a calibration motion for acquiring the parameter expressing at least one of an attachment orientation and an attachment position in the one leg of the sensor unit and a posture of the one leg in standing on the one leg, generates a reproduction image where a motion state of the leg during the exercise is reproduced in pseudo manner based on data output from the sensor unit in a case where the human body performs exercise of moving the leg and the parameter, and displays an image including at least the reproduction image as exercise information on the display unit.

17 Claims, 23 Drawing Sheets

(51) Int. Cl.
*G06Q 10/06* (2012.01)
*A61B 5/11* (2006.01)

(52) U.S. Cl.
CPC ..... *G06F 19/3481* (2013.01); *G06Q 10/0639* (2013.01); *A61B 2560/0209* (2013.01); *A61B 2560/0223* (2013.01)

(56) References Cited

U.S. PATENT DOCUMENTS

| | | | |
|---|---|---|---|
| 9,999,376 B2 | 6/2018 | Chan et al. | |
| 2005/0234309 A1 | 10/2005 | Klapper | |
| 2008/0091373 A1 | 4/2008 | McGibbon et al. | |
| 2009/0322763 A1* | 12/2009 | Bang | G06F 3/011 345/474 |
| 2012/0130280 A1* | 5/2012 | Lee | A61B 5/0004 600/587 |
| 2013/0041291 A1 | 2/2013 | Soubeyrat et al. | |
| 2014/0128778 A1 | 5/2014 | Chan et al. | |

FOREIGN PATENT DOCUMENTS

| | | |
|---|---|---|
| JP | 2012120579 A | 6/2012 |
| WO | 2014071208 A1 | 5/2014 |

OTHER PUBLICATIONS

Japanese Office Action dated Aug. 24, 2018 (and an English translation thereof) issued in counterpart Japanese Application No. 2014-251931.

* cited by examiner

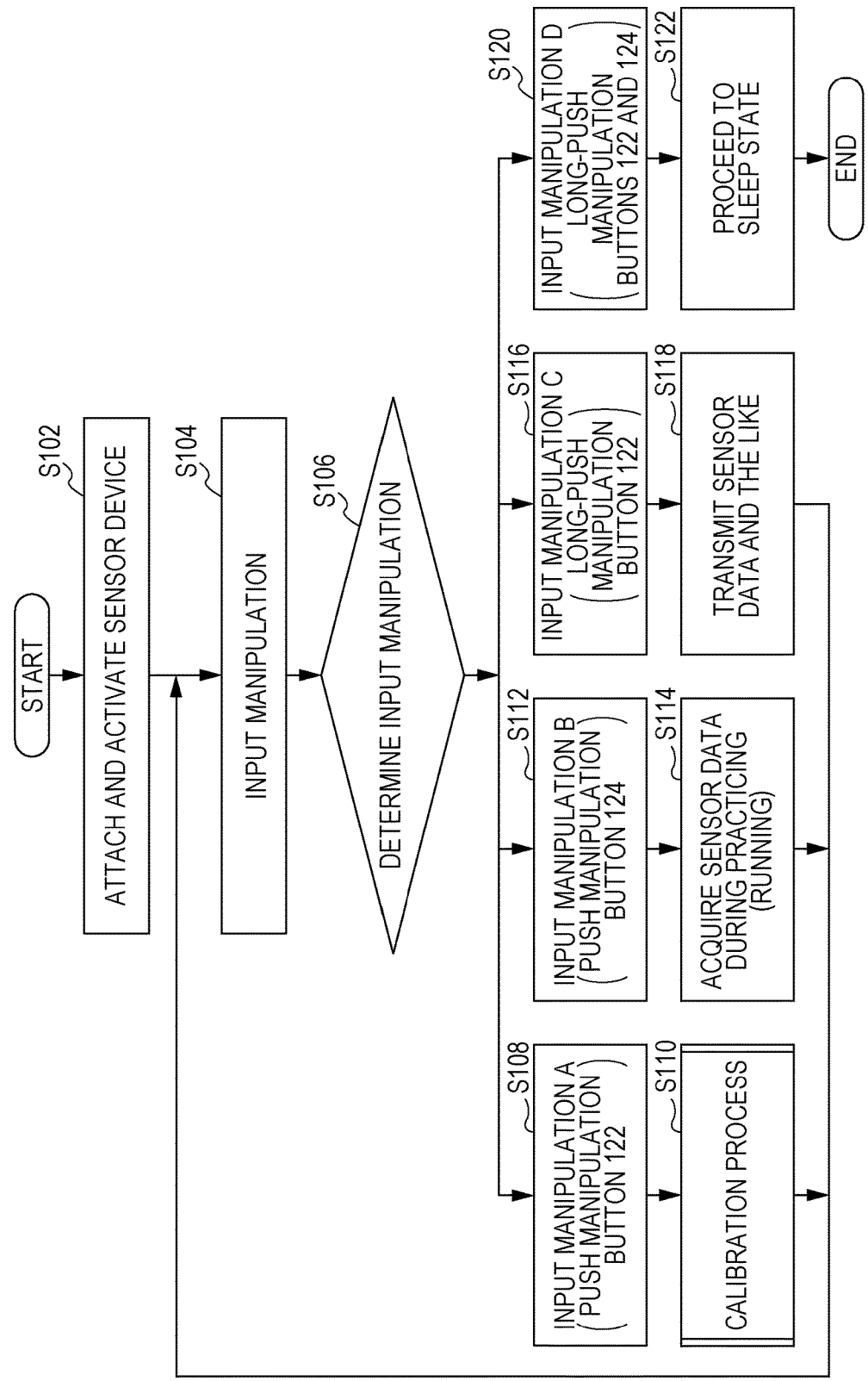

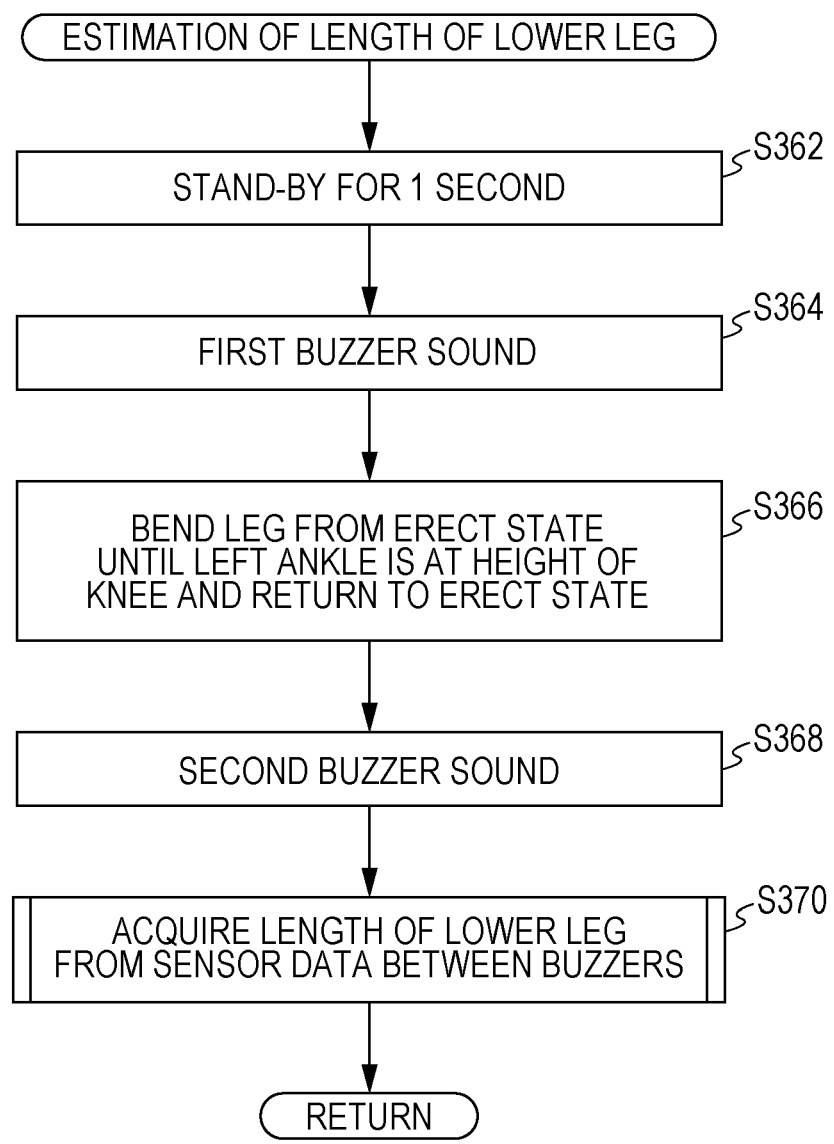

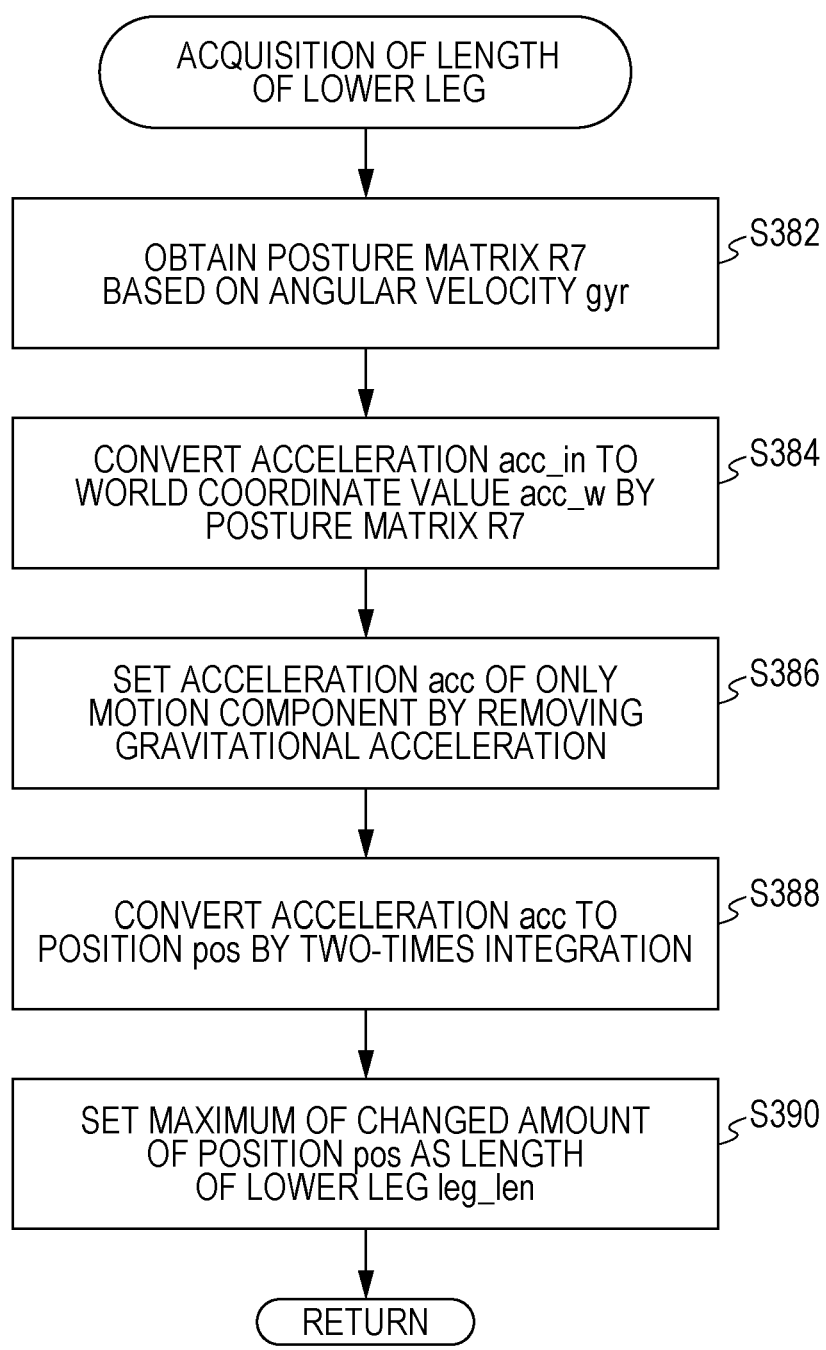

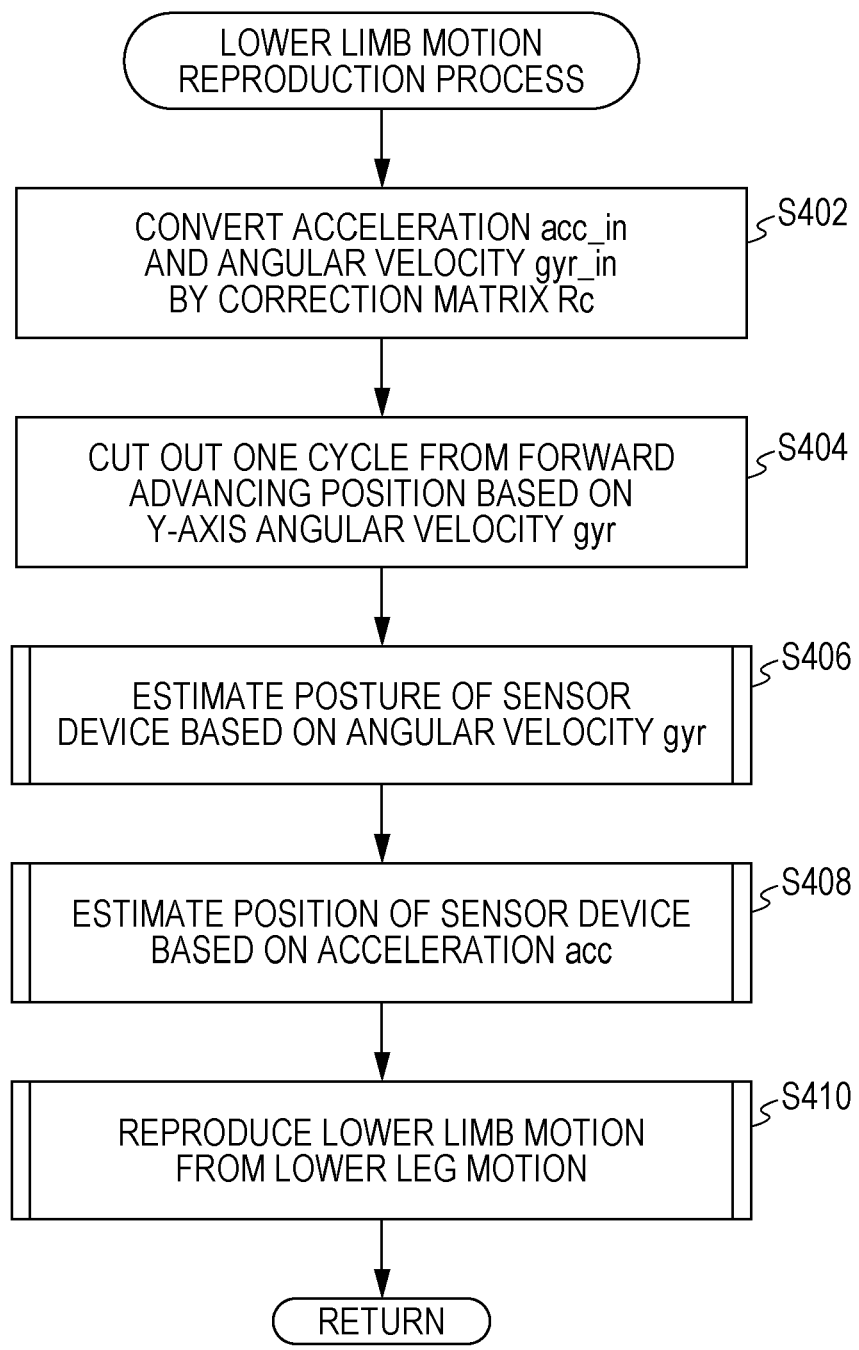

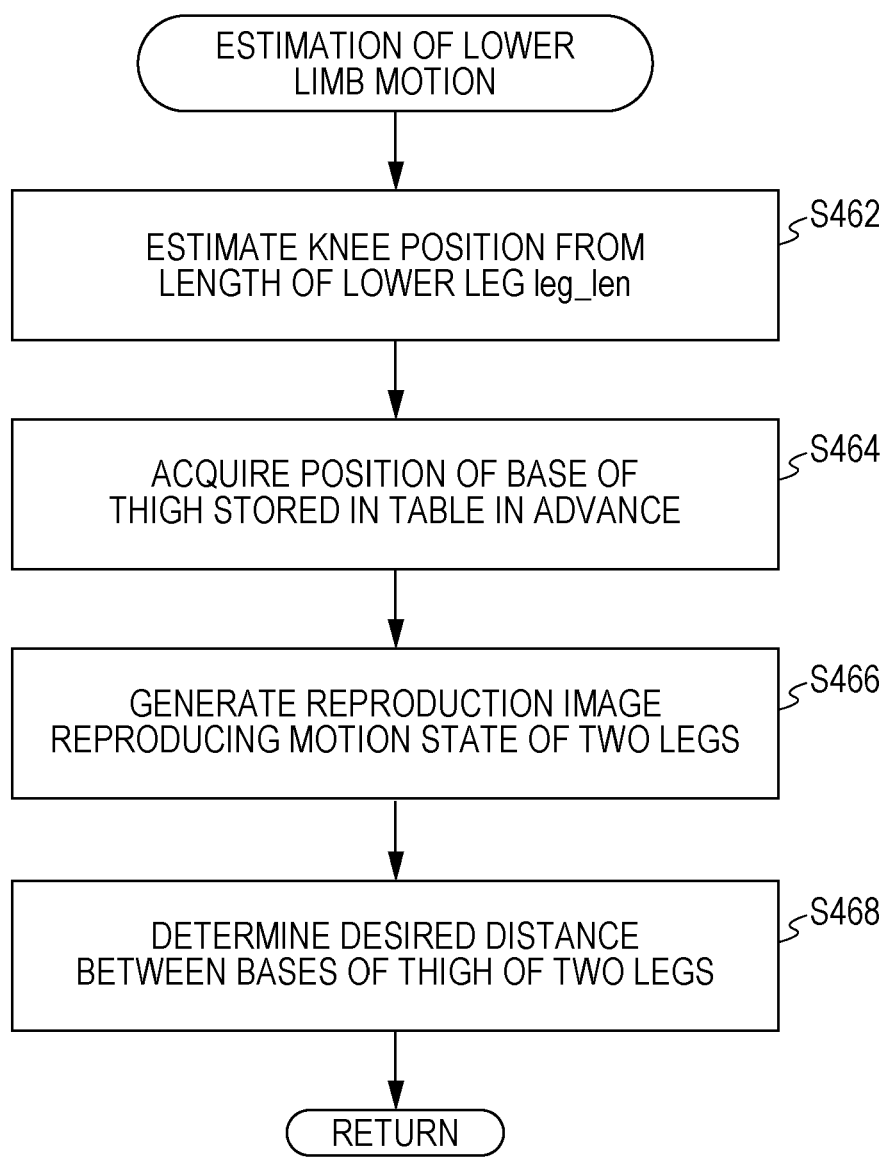

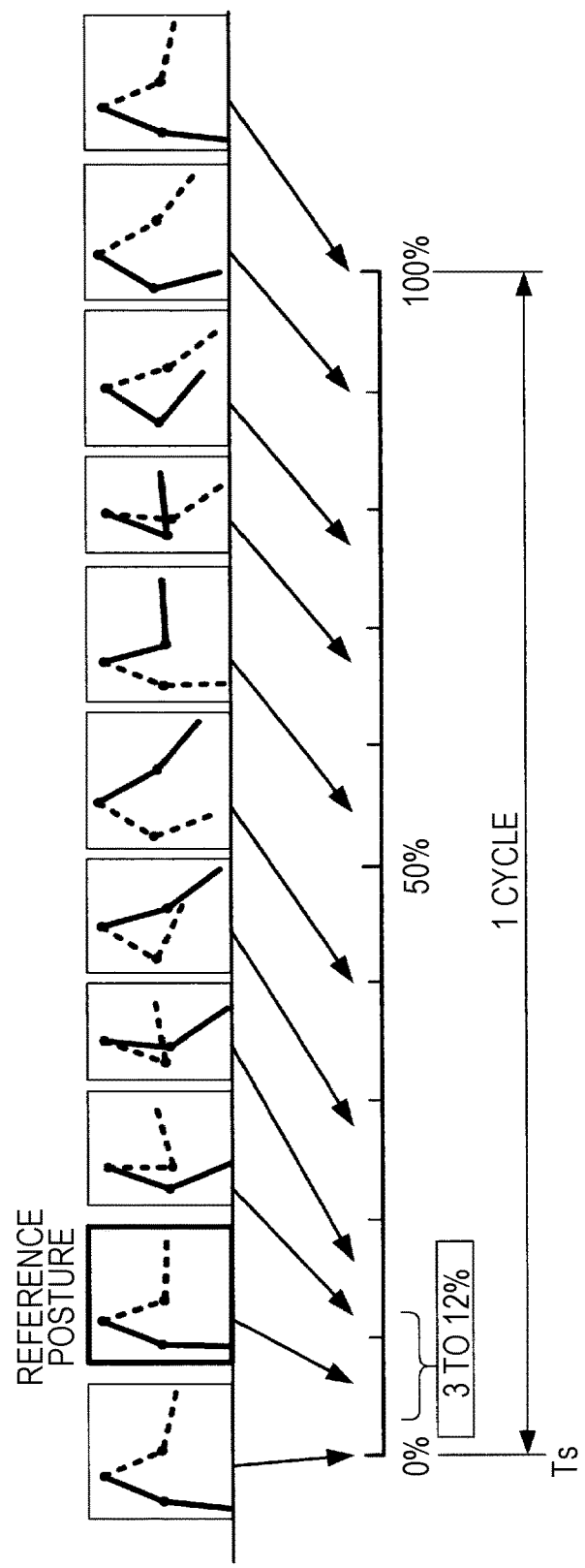

FIG. 19

| FRAME | LENGTH OF LOWER LEG | | | | |
|---|---|---|---|---|---|
| | LESS THAN 200mm | 200mm OR MORE AND LESS THAN 210mm | | 790mm OR MORE AND LESS THAN 800mm | 800mm OR MORE |
| 1 | (100, 500, 0) | (100, 500, 0) | | (200, 1695, 0) | (200, 1700, 0) |
| 2 | (100, 498, −1) | (100, 498, −1) | | (200, 1693, −3) | (200, 1698, −3) |
| 3 | (100, 497, −2) | (100, 497, −2) | ..... | (200, 1689, −6) | (200, 1694, −6) |
| 4 | (100, 496, 3) | (100, 496, 3) | | (200, 1685, −9) | (200, 1690, −9) |
| 5 | (100, 595, −3) | (100, 595, −3) | | (200, 1680, −12) | (200, 1685, −12) |
| 6 | (100, 494, −3) | (100, 494, −3) | | (200, 1675, −16) | (200, 1680, −16) |
| 7 | (100, 493, −3) | (100, 493, −3) | | (200, 1665, −20) | (200, 1670, −20) |
| 8 | (100, 491, 4) | (100, 491, 4) | | (200, 1650, −25) | (200, 1655, −25) |
| ⋮ | ⋮ | ⋮ | | ⋮ | ⋮ |
| 149 | (100, 505, 2) | (100, 505, 2) | ..... | (200, 1700, 2) | (200, 1705, 2) |
| 150 | (100, 502, 1) | (100, 502, 1) | | (200, 1698, 1) | (200, 1702, 1) |

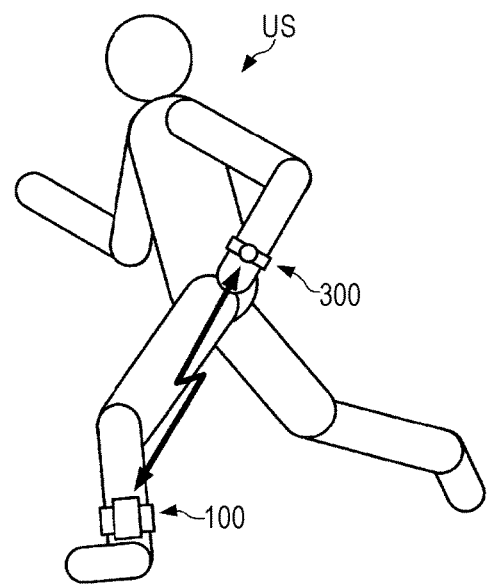
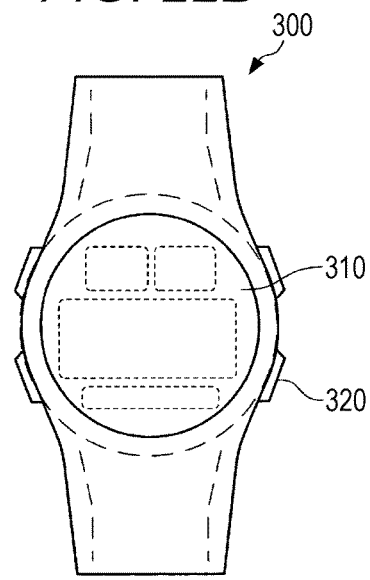
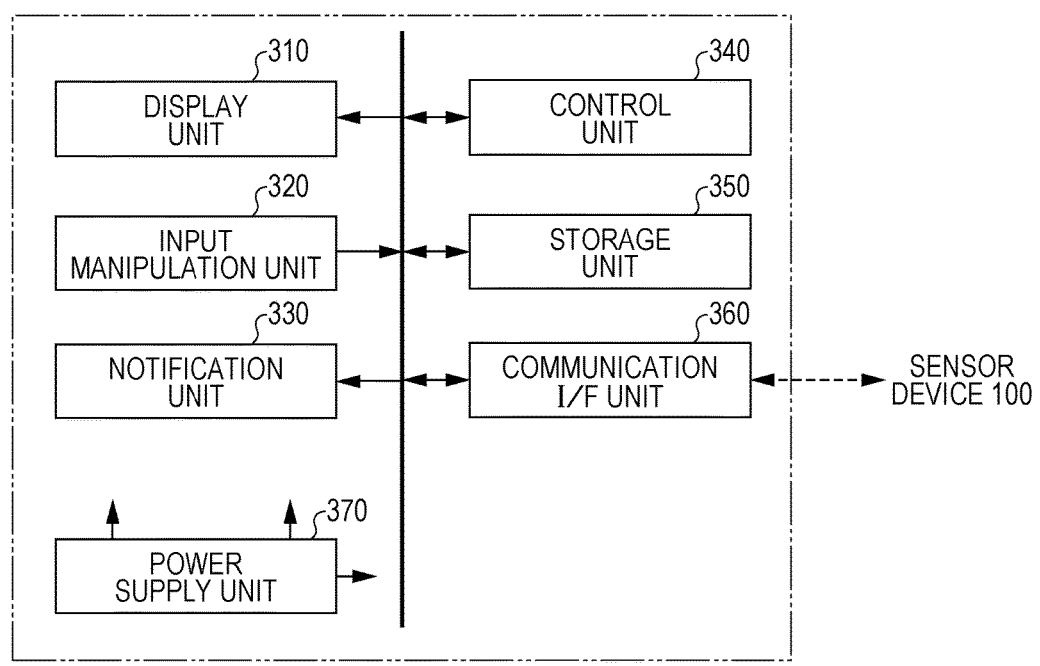

EXERCISE INFORMATION DISPLAY SYSTEM, EXERCISE INFORMATION DISPLAY METHOD AND COMPUTER-READABLE RECORDING MEDIUM

CROSS-REFERENCE TO RELATED APPLICATIONS

The present invention contains subject matter related to Japanese Patent Application No. 2014-251931 filed in the Japanese Patent Office on Dec. 12, 2014, the entire contents of which are incorporated herein by reference.

BACKGROUND OF THE INVENTION

1. Field of the Invention

The present invention relates to an exercise information display system and an exercise information display method capable of allowing a user to simply and precisely determine an exercise state, and a computer-readable recording medium storing an exercise information display program.

2. Description of the Related Art

In recent years, as health consciousness increases, an increasing number of people do exercise such as running, walking, or cycling every day to maintain or improve health state. In addition, an increasing number of people also make a further full-scale training for the purpose of participating in various games, competitions, or the like.

These people have much awareness and a high interest in measuring or recording their own health state or exercise state as numerical values or data.

In order to meet these demands, in recent years, products or techniques of determining a motion of a body by using a motion sensor capable of measuring acceleration or angular velocity have been studied. For example, Japanese Patent Application Publication No. 2012-000343 discloses a walking analysis system where a measurement sensor is installed to sandwich hip joints, knee joints, or ankle joints and acceleration or angular velocity during the walking is measured, so that joint angles of the joints or other walking information are determined to perform estimation of the walking state.

In the technique disclosed in the above Document or the like, in order to determine a motion of a lower limb during the exercise to reproduce the motion state, motion sensors of a hip, a thigh, and a lower leg are configured to be installed to measure acceleration, angular velocity, or the like according to each motion. Therefore, a large number of the motion sensors need to be attached to the body, trouble thereof is very complicated, and construction of the system costs higher. Therefore, ordinary persons cannot easily use the system.

BRIEF SUMMARY OF THE INVENTION

The present invention has an advantage in that it is possible to provide an exercise information display system, an exercise information display method capable of precisely determining an exercise state, and a computer-readable recording medium storing an exercise information display program, thus, accurately reproducing the exercise state of the user by a simple configuration where a sensor unit is attached to only one ankle of a user.

According to an embodiment of the present invention, there is provided an exercise information display system including: a sensor unit which is attached to an ankle of one leg of a human body and outputs data on a motion state of the one leg; a display unit; and a control unit which processes the data, wherein the control unit performs: acquiring the data as calibration data in a case where the human body performing a calibration motion for acquiring a parameter expressing at least one of an attachment orientation of the sensor unit, an attachment position of the sensor unit on the one leg, and a posture of the one leg in standing on the one leg, acquiring the parameter based on the calibration data, acquiring the data as exercise data in a case where the human body performing exercise of moving at least the one leg, generating a reproduction image where a motion state of the leg during the exercise is reproduced in a pseudo manner based on the exercise data and the parameter, and displaying an image including at least the reproduction image as exercise information on the display unit.

According to another embodiment of the present invention, there is provided an exercise information display method including the steps of: acquiring data output from a sensor unit as calibration data attached to an ankle of one leg of a human body in a case where the human body performs a calibration motion for acquiring a parameter expressing at least one of an attachment orientation of the sensor unit, an attachment position of the sensor unit on the one leg, and a posture of the one leg in standing on the one leg; acquiring the parameter based on the calibration data; acquiring the data as exercise data in a case where the human body performs exercise of moving at least the one leg; generating a reproduction image where a motion state of the leg during the exercise is reproduced in a pseudo manner based on the exercise data and the parameter; and displaying an image including at least the reproduction image as exercise information on a display unit.

According to still another embodiment of the present invention, there is provided a non-transitory computer-readable recording medium storing an exercise information display program for causing a computer to execute, wherein the exercise information display program causes the computer to execute: acquiring data from a sensor unit as calibration data attached to an ankle of one leg of the human body in a case where the human body performs a calibration motion for acquiring a parameter expressing at least one of an attachment orientation of the sensor unit, an attachment position of the sensor unit on the one leg, and a posture of the one leg in standing on the one leg, acquiring the parameter based on the calibration data; acquiring the data as exercise data in a case where the human body performs exercise of moving at least the one leg, generating a reproduction image where a motion state of the leg during the exercise is reproduced in a pseudo manner based on the exercise data and the parameter; and displaying an image including at least the reproduction image as exercise information on a display unit.

BRIEF DESCRIPTION OF THE SEVERAL VIEWS OF THE DRAWING

FIG. 3 is a flowchart illustrating an example of a control method (exercise information measuring operation) in the sensor device applied to the exercise information display system according to one embodiment;

FIG. 8 is a flowchart illustrating an example of a lower limb length estimation process executed in the calibration process applied to one embodiment;

FIG. 9 is a flowchart illustrating an example of a lower limb length acquisition method (lower limb length acquisition process) executed in the lower limb length estimation process applied to one embodiment;

FIG. 12 is a flowchart illustrating an example of a lower limb motion reproduction process applied to the exercise information display system according to one embodiment;

FIG. 15 is a flowchart illustrating an example of a lower limb motion estimation process executed in the lower limb motion reproduction process applied to one embodiment;

FIG. 18 is a schematic diagram illustrating a position of a reference posture of one cycle of running motion in the lower limb motion reproduction process applied to one embodiment;

FIG. 19 is a schematic diagram illustrating an example of a table of a relationship of correspondence between a lower leg length and a motion of a base of a thigh referred to in the lower limb motion reproduction process applied to one embodiment;

FIGS. 22A, 22B, and 22C are schematic configurational diagrams illustrating a modified example of the exercise information display system according to one embodiment.

DETAILED DESCRIPTION OF THE INVENTION

Hereinafter, embodiments of an exercise information display system and an exercise information display method according to the present invention will be described in detail with reference to the drawings.

In addition, in the below description, the case where a user does an exercise such as running will be described.

<Exercise Information Display System>

Figure 1A:
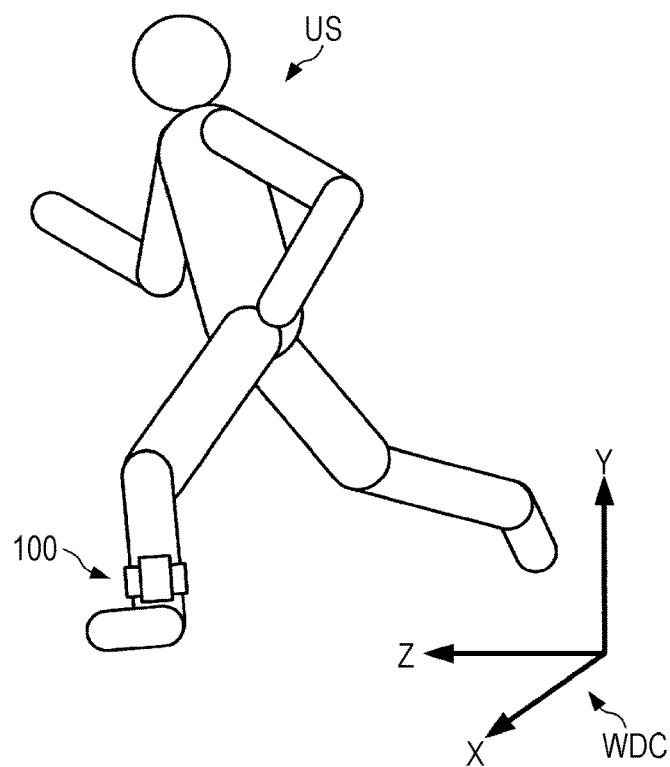
FIGS. 1A, 1B, and 1C are schematic configurational diagrams illustrating an embodiment of an exercise information display system according to the present invention.
Figure 1C:
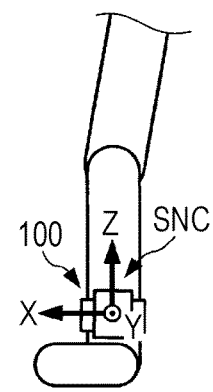
Figure 1B:
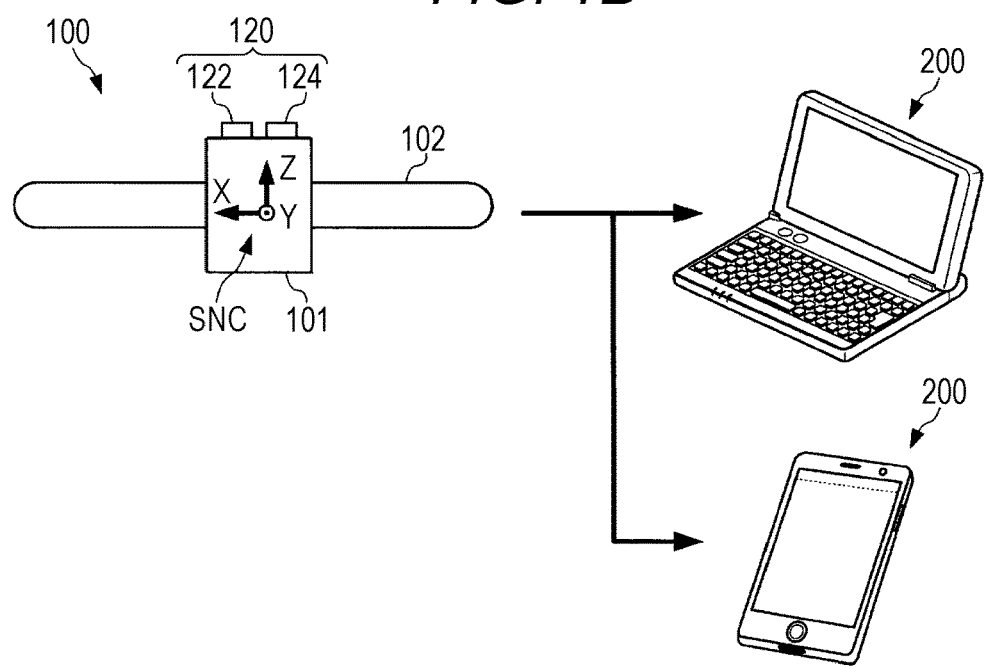

FIGS. 1A, 1B, and 1C are schematic configurational diagrams illustrating an embodiment of an exercise information display system according to the present invention. FIG. 1A is a schematic diagram illustrating an example of attachment of a sensor device on a human body, which is applied to the exercise information display system. FIG. 1B is a schematic diagram illustrating a whole configuration of the exercise information display system. FIG. 1C is a schematic diagram illustrating a coordinate system (sensor coordinate system) in a sensor device.

Figure 2A:
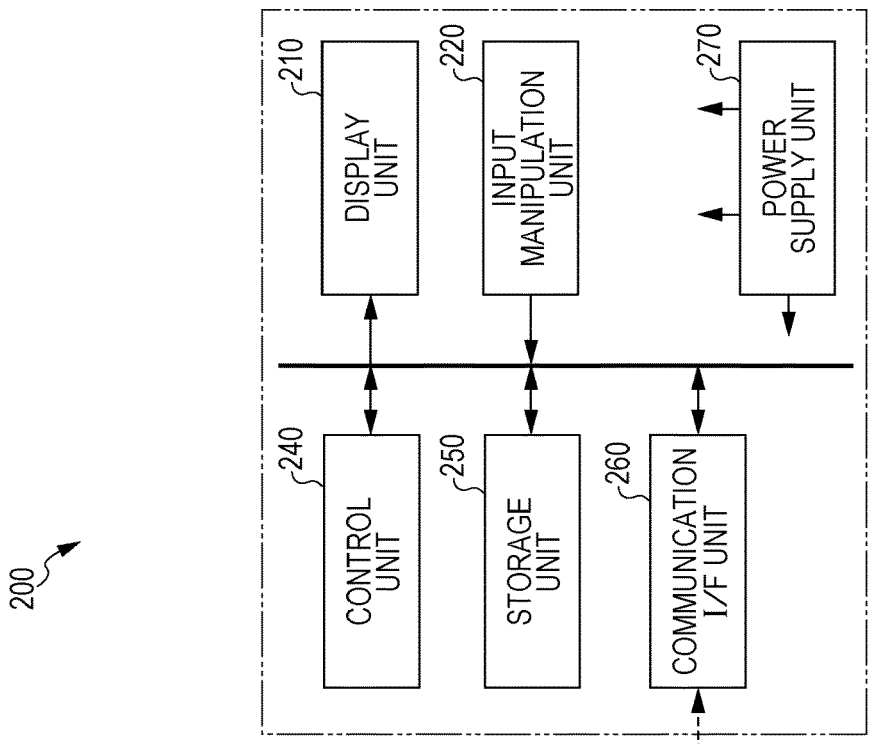
FIGS. 2A and 2B are schematic block diagrams illustrating a configurational example of an sensor device and an information processing device applied to the exercise information display system according to one embodiment.
Figure 2B:
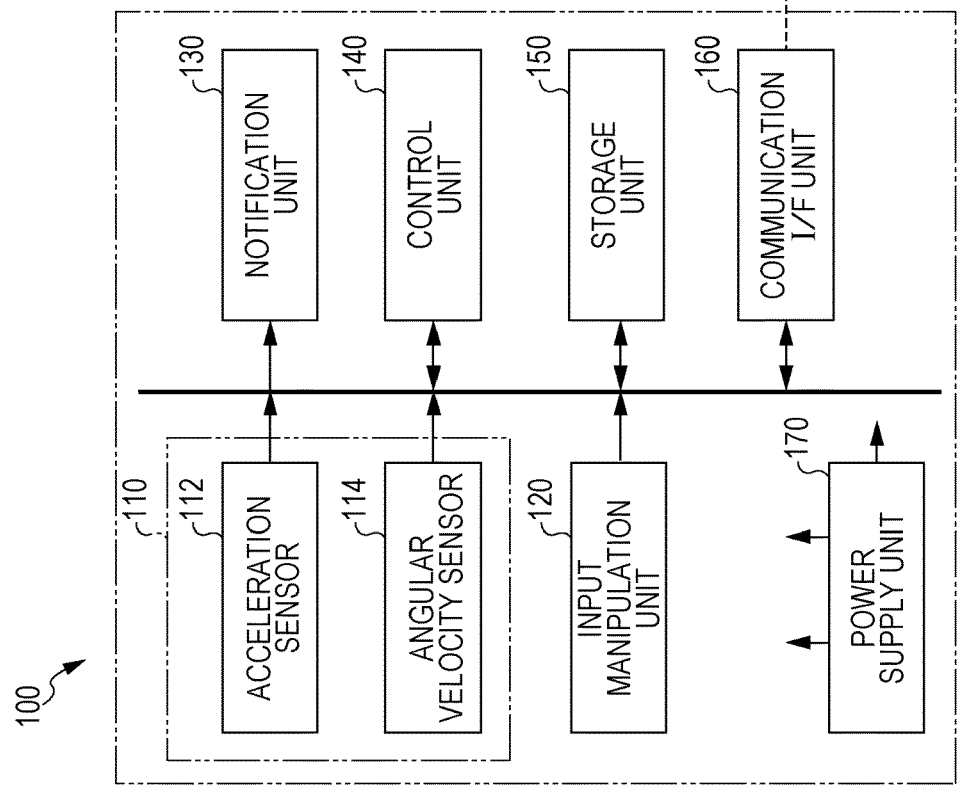

FIGS. 2A and 2B are schematic block diagrams illustrating a configurational example of a sensor device and an information processing device applied to the exercise information display system according to the embodiment.

For example, as illustrated in FIGS. 1A and 1B, the exercise information display system according to the embodiment is configured to include a sensor device 100 which the user US as a measurement object attached to a body and an information processing device 200 which reproduces in a pseudo manner an exercise state based on sensor data and the like acquired from the sensor device 100 and visibly provides the exercise state to the user.

(Sensor Device 100)

As illustrated in FIG. 1A, the sensor device 100 is attached to an ankle of one leg of the user US or in the vicinity of the ankle.

For example, as illustrated in FIG. 1B, the sensor device 100 has an outer appearance mainly including a device main body 101 including various sensors detecting an exercise state of the user US and a belt unit 102 winding around the ankle of one leg of the user US to attach the device main body 101 on the ankle.

In addition, in FIGS. 1A and 1B, as a configuration of the sensor device 100, the case where the device main body 101 is attached by winding the belt unit 102 on the ankle of one leg of the user US is described.

However, the invention is not limited thereto. Namely, with respect to the sensor device 100, if a sensor device has a structure to be attached to a predetermined site (herein, in the vicinity of the ankle) of the body of the user US without occurrence of irregularity, the sensor device may have a different configuration.

For example, the sensor device may not include the above-described belt unit 102, and the sensor device may have a configuration where the sensor device is attached by adhering to shoes or clothing (wear, socks, or the like) which is worn by the user US, being embedded inside, or being sandwiched by a clip or the like.

More specifically, for example, as illustrated in FIG. 2A, the sensor device 100 is mainly configured to include a sensor unit 110, an input manipulation unit 120, a notification unit 130, a control unit (calibration process unit) 140, a storage unit 150, a communication interface unit (hereinafter, referred to as a "communication I/F unit") 160, and a power supply unit 170.

The sensor unit 110 includes motion sensors for detecting a motion of a human body. As illustrated in FIG. 2A, the sensor unit includes at least an acceleration sensor 112 and an angular velocity sensor (gyro sensor) 114.

The acceleration sensor 112 measures a rate of change in motion velocity (acceleration of a translation motion) during the exercise of the user US and outputs acceleration data (acceleration signals) in three perpendicular axis directions The angular velocity sensor 114 measures a rate of change in motion orientation (rotational angular velocity) during the exercise of the user US and outputs angular velocity data (angular velocity signals) in three perpendicular axis directions.

The acceleration sensor 112 and the angular velocity sensor 114 perform measurement every set sampling interval. The sampling interval is set to, for example, 5 msec or about thereof.

Sensor data (acceleration data, angular velocity data) are measured and output by the sensor unit 110 at least when the user US does exercise of moving one leg attached with the sensor device 100, and the sensor data are stored in a predetermined storage area of the later-described storage unit 150.

Herein, a sensor coordinate SNC of the acceleration sensor 112 and the angular velocity sensor 114 is a relative coordinate, and for example, as illustrated in FIG. 1C, on the basis of an attachment position of the sensor device 100, a direction toward the knee (upward direction in the figure) is set as the +Z axis direction, an advancement direction in the erect state (leftward direction in the figure) is set as the +X axis direction, and a left-handed direction in the erect state (frontward direction in the figure) is set as the +Y axis direction.

In contrast, a world coordinate WDC is an absolute coordinate, and as illustrated in FIG. 1A, an advancement direction during the pacing (leftward direction in the figure) is set as the +Z axis direction, a left-handed direction during the pacing (frontward direction in the figure) is set as the +X axis direction, and a direction vertical to the group (upward direction in the figure) is set as the +Y axis direction. Herein, the −Y axis direction in the world coordinate WDC corresponds to the gravity direction (direction of the gravitational acceleration).

For example, as illustrated in FIG. 1B, the input manipulation unit 120 includes manipulation buttons (push buttons) 122 and 124 and a switch such as a slide button or a touch button which are installed on a side surface, a front surface, or the like of the device main body 101.

The input manipulation unit 120 is used, for example, for power manipulation for activating the sensor device 100 and manipulation for setting an operation mode of the sensor device 100.

Although not shown, the notification unit 130 includes a sound unit such as a buzzer or a speaker, a vibration unit such as a vibration motor or a vibrator, a light emitting unit of a light emitting device or the like such as an LED, which is installed in the device main body 101.

The notification unit 130 provides and notifies at least the later-described information on procedure in the calibration process for predetermined parameters or information on operation abnormality of the sensor device 100 to the user through visual perception, auditory perception, tactile perception, and the like.

In addition, the notification unit 130 may include at least one of the sound unit, the vibration unit, the light emitting unit, and the like or a combination of the plural units.

The control unit 140 is a processing unit such as a CPU (central processing unit) or an MPU (microprocessor) having a timing function and executes a predetermined control program or algorithm program on the basis of an operation clock.

Thus, the control unit 140 controls various operations such as a calibration process for a predetermined parameter, a sensing operation of the sensor device 100, a notification operation of the notification unit 130, and a transmission operation for the sensor data or the like in the communication I/F unit 160.

Herein, in the embodiment, when the user US performs predetermined input manipulation by using the input manipulation unit 120, the control unit 140 sets a predetermined operation mode and executes an operation according to the operation mode.

In addition, the operation in each operation mode will be described later.

The storage unit 150 stores the sensor data or the like acquired from the above-described sensor unit 110 in association with time data in a predetermined storage area.

When the control unit 140 executes a predetermined program, the storage unit 150 stores various data or information used or generated in the calibration process for a predetermined parameter, the sensing operation of the sensor unit 110, the transmission operation for the sensor data in the communication I/F unit 160, or the like.

The storage unit 150 further stores the control program or the algorithm program executed in the control unit 140.

In addition, the program executed in the control unit 140 may be incorporated in the control unit 140 in advance.

A portion or entire portions of the storage unit 150 may have a form of a removable storage medium such as a memory card or may be configured to be detachable to the sensor device 100.

The communication I/F unit 160 functions as an interface at the time of transmitting/receiving the sensor data (acceleration data, angular velocity data) acquired from the sensor unit 110, various data or information generated in the later-described calibration process, or the like to/from the information processing device 200.

Herein, as a method of transmitting/receiving the sensor data or the like between the sensor device 100 and the information processing device 200 through the communication I/F unit 160, for example, various wireless communication methods or wired communication methods may be applied.

Herein, in the communication I/F unit 160, in the case of transmitting/receiving the sensor data or the like in the wireless communication method, for example, Bluetooth (registered trademark) as a local area wireless communication standard for a digital device, Bluetooth (registered trademark) low energy (LE) set as a low power consumption type communication, NFC (Near field communication), or equivalent communication methods can be applied well.

The power supply unit 170 supplies driving power to each component of the sensor device 100. As the power supply unit 170, for example, a commercially available primary battery such as a button cell or a commercially available secondary battery such as a lithium ion battery is applied.

Besides the above-described primary battery or secondary battery, as the power supply unit 170, power sources according to an energy harvesting technique for generating electricity by energy of vibration, light, heat, electromagnetic waves, or the like alone or in combination with other power sources.

(Information Processing Device 200)

After the end of the exercise of the user US, the information processing device 200 reproduces in a pseudo manner the exercise state (particularly, the motion state of the lower limb) of the body based on the sensor data or the like transmitted from the sensor device 100 and provides the reproduced exercise state to the user US in a predetermined display form.

Herein, the information processing device 200 includes at least a display unit and has a function of capable of executing a predetermined program (exercise information display program) for reproducing in a pseudo manner the motion state of the lower limb described later. As illustrated in FIG. 1B, the information processing device 200 may be a notebook type personal computer or desktop type personal computer or may be a mobile information terminal such as a smartphone (highly-functional mobile phone) or a tablet terminal.

In the case where the information processing device 200 executes an exercise information display program for reproducing the motion state of the lower limb by using a server computer (so called, a cloud system) on a network, the information processing device 200 may have a function of connecting to the network and may be a communication terminal having a network information browsing software.

More specifically, for example, as illustrated in FIG. 2B, the information processing device 200 is mainly configured to include a display unit 210, an input manipulation unit 220, a control unit (motion reproduction process unit) 240, a storage unit 250, a communication I/F unit 260, and a power supply unit 270.

The display unit 210 includes, for example, a liquid crystal type or light-emitting type display panel and displays at least information associated with the input manipulation using the input manipulation unit 220 or the exercise state (motion state of the lower limb) reproduced in a pseudo manner based on the sensor data or the like in a predetermined form.

The input manipulation unit 220 is an input unit such as a keyboard, a mouse, a touch pad, or a touch panel attached to the information processing device 200. The input manipulation unit 220 is used at the time of executing a function corresponding to an icon, a menu, or a position by selecting an arbitrary icon or menu displayed on the display unit 210 or indicating an arbitrary position in a displayed screen.

The control unit 240 is a processing unit such as a CPU or an MPU and executes a predetermined control program or a predetermined algorithm program to control a process of reproducing the motion state of the lower limb during the exercise of the user US and various operations of the display operation of the display unit 210 and the reception operation of the sensor data or the like in the communication I/F unit 260.

The storage unit 250 stores the sensor data or the like transmitted from the sensor device 100 through the communication I/F unit 260 in a predetermined storage area. When the control unit 240 executes a predetermined program, the storage unit 250 stores various data or information used or generated in the process of reproducing the motion state of the lower limb during the exercise of the user US, the display operation of the display unit 210, the reception operation of the sensor data or the like in the communication I/F unit 260.

The storage unit 250 further stores the control program or the algorithm program executed in the control unit 240.

In addition, the program executed in the control unit 140 may be built in the control unit 140 in advance.

A portion or entire portions of the storage unit 250 may have a form of a removable storage medium such as a memory card or may be configured to be detachable to the information processing device 200.

The communication I/F unit 260 functions as an interface at the time of transmitting/receiving the sensor date acquired from the sensor device 100, various data or information generated in the calibration process, or the like. Herein, as a method of transmitting/receiving the sensor data or the like between the information processing device 200 and the sensor device 100 through the communication I/F unit 260, as described above, various wireless communication methods or wired communication methods may be applied.

The power supply unit 270 supplies driving power to each component of the information processing device 200. As the power supply unit 270, a secondary battery such as a lithium ion battery or a commercial AC power source is applied for a mobile electronic device such as a smartphone, a tablet terminal, or a notebook type personal computer. In the case where the information processing device 200 is a desktop type personal computer, as the power supply unit 270, a commercial AC power source is applied.

<Exercise Information Display Method>

Next, the control method (exercise information display method) in the exercise information display system according to the embodiment will be described with reference to the drawings.

FIG. 3 is a flowchart illustrating an example of a control method (exercise information measuring operation) in the sensor device applied to the exercise information display system according to the embodiment.

Figure 4:
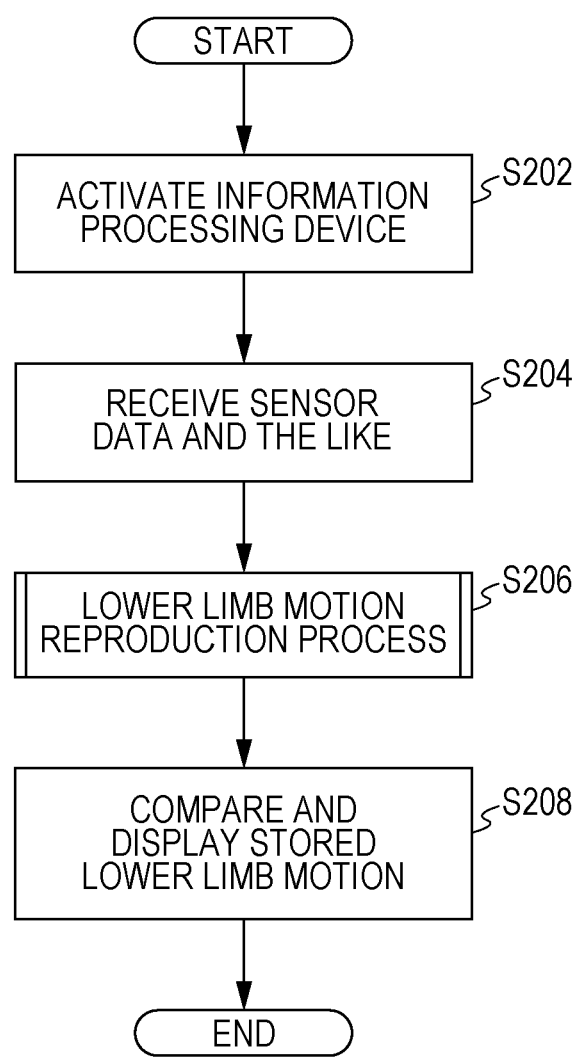
FIG. 4 is a flowchart illustrating an example of a control method (exercise information reproducing operation) in the information processing device applied to the exercise information display system according to one embodiment.

FIG. 4 is a flowchart illustrating an example of a control method (exercise information reproducing operation) in the information processing device applied to the exercise information display system according to the embodiment.

In the exercise information display system according to the embodiment, the exercise information measuring operation of the sensor device 100 illustrated in the flowchart of FIG. 3 and the exercise information reproducing operation of the information processing device 200 illustrated in the flowchart of FIG. 4 are mainly executed.

Herein, a series of the control methods in the following operations are realized by the sensor device 100 and the information processing device 200 executing predetermined programs.

In the exercise information measuring operation of the sensor device 100, as illustrated in FIG. 3, first, the user US attaches the sensor device 100 to the body and activates the sensor device 100 (step S102).

More specifically, the user US attaches the device main body 101 to a predetermined position, for example, by winding the belt unit 102 of the sensor device 100 on the left ankle.

Next, the user US performs power-on manipulation on a power switch (input manipulation unit 120) of the device main body 101, so that driving power is supplied from the power supply unit 170 to each component of the sensor device 100, and thus, the sensor device 100 is activated.

In addition, in the sensor device 100, a battery power source (primary battery or charged secondary battery) may be attached to the power supply unit 170 supply the driving power from the power supply unit 170 to each component, so that the sensor device 100 may be set in a constantly activated state.

In this case, when the state that the sensing operation, the input manipulation, or the like is not performed continues for a predetermined time after the driving power is supplied from the power supply unit 170, it is preferable that the sensor device 100 proceed to a sleep state or the like so as to reduce power consumption.

Next, the user US manipulates the manipulation buttons 122 and 124 of the input manipulation unit 120 installed to the device main body 101 (step S104), so that the sensor device 100 is set to a predetermined operation state (operation mode).

Next, the control unit 140 determines the manipulation state of the input manipulation unit 120 by the user US (step S106) to set the operation mode according to the manipulation state.

More specifically, in the case where the control unit 140 determines that, for example, the manipulation button 122 of the input manipulation unit 120 is pushed by the user US (input manipulation A) (step S108), the control unit controls the sensor device 100 to proceed to the calibration mode, and the calibration process for a predetermined parameter is executed (step S110).

The control unit 140 controls various data or information generated by the calibration process to be stored in the predetermined storage area of the storage unit 150. In addition, the calibration process will be described later.

In the case where the control unit 140 determines that, for example, the manipulation button 124 is pushed by the user US (input manipulation B) (step S112), and the control unit controls the sensor device 100 to proceed to the measurement mode.

Next, the control unit controls the sensor unit 110 to start the sensing operation to acquire the sensor data (acceleration data, angular velocity data) during the exercise (practicing) of the user US and controls the acquired sensor data in association with time data to be stored in the predetermined storage area of the storage unit 150 (step S114).

In addition, in the case where the manipulation button 124 is pushed by the user US again during the measurement mode, the control unit 140 ends the measurement mode.

In the case where the control unit 140 determines that, for example, the manipulation button 122 is long-pushed for 5 seconds or more by the user US (input manipulation C) (step S116), the control unit controls the sensor device 100 to proceed to the communication mode.

Next, the control unit controls the sensor data during the exercise stored in the storage unit 150 or various data or information generated by the calibration process to be transmitted to the information processing device 200 according to a predetermined communication method (step S118).

In addition, the communication mode is generally set after the end of the exercise by the user US, and the sensor data or the like stored in the storage unit 150 are transmitted to the information processing device 200. For this reason, when the sensor device 100 is in this communication mode, the sensor device may not be attached to the body (ankle) of the user US.

In the case where the control unit 140 determines that, for example, the manipulation buttons 122 and 124 are simultaneously long-pushed by the user US (input manipulation D) (step S120), the control unit controls the sensor device 100 to proceed to the sleep mode so that the sensor device 100 is operated in a low power consumption state (step S122).

Next, as illustrated in the flowchart of FIG. 3, after the calibration process in the calibration mode (step S110), the sensor data acquisition operation in the measurement mode (step S114), and the transmission operation for the sensor data or the like in the communication mode (step S118) among the above-described operation modes, the control unit 140 returns to step S104 to wait for the next input manipulation of the user US (stand by).

At this time, after the end of the above-described process operations (the calibration process, the sensor data acquisition operation, and the transmission operation for the sensor data or the like), the control unit 140 may allow the sensor device 100 to proceed to the sleep mode to set the sensor device 100 to the state where the sensor device is operated in the low power consumption state so as to wait for the next input manipulation of the user US.

In the case where the low power consumption operation in the sleep mode (step S122) among the above-described operation modes continues for a predetermined time, the control unit 140 ends the exercise information measuring operation of the sensor device 100.

At this time, after the sensor device 100 is allowed to proceed to the sleep state, the control unit 140 may turn to step S104 so as to wait for the next input manipulation of the user US.

In addition, although not shown in the flowchart illustrated in FIG. 3, the control unit 140 constantly monitors input manipulation of stopping or ending a process operation or a change of the operation state during the execution of a series of the process operations in the sensor device 100, and in the case where the input manipulation or the change of the state is detected, the control unit forcibly ends the process operation.

More specifically, when the control unit 140 detects power-off manipulation of the power switch by the user US, a decrease in remaining amount of battery in the power supply unit 170, or abnormality of function or application during the execution of the process operation, the control unit forcibly stops and ends a series of the process operations.

As illustrated in FIG. 4, with respect to an exercise information reproducing operation in the information processing device 200, first, the user US performs power-on manipulation on the power switch (input manipulation unit 220) of the information processing device 200, so that driving power is supplied from the power supply unit 270 to each component of the information processing device 200, and thus, the information processing device 200 is activated (step S202).

Next, by the user US manipulating the input manipulation unit 120 of the sensor device 100, the control unit 240 receives the sensor data or the like transmitted from the sensor device 100 set to the communication mode according to a predetermined communication method through the communication OF unit 260 (step S204).

Herein, the sensor data acquired during the exercise or various data or information generated by the calibration process which are transmitted from the sensor device 100 are stored in the predetermined storage area of the storage unit 250.

Next, the control unit 240 executes a lower limb motion reproduction process of reproducing in a pseudo manner the motion state of the lower limb during the exercise of the user US based on the sensor data (acceleration data and angular velocity data) and various data or information generated by the calibration process which are transmitted from the sensor device 100 (step S206).

In addition, the process of reproducing in a pseudo manner the motion state of the lower limb of the user US will be described later.

Next, the control unit 240 controls the currently reproduced motion state of the lower limb of the user US, the motion state of the lower limb during the previous exercise of the user US stored in advance in the storage unit 250, or the motion states of lower limbs of athletes having a form over an arbitrary level to be displayed on the display unit 210 in a comparable form (step S208).

Thus, by viewing the comparison animation displayed on the display unit 210, the user US can precisely determine the motion state during the exercise and can reflect on the subsequent training or the like.

(Calibration Process)

Next, the calibration process executed in the control method (exercise information measuring operation) of the above-described exercise information display system will be described in detail with reference to the drawings.

Figure 5:
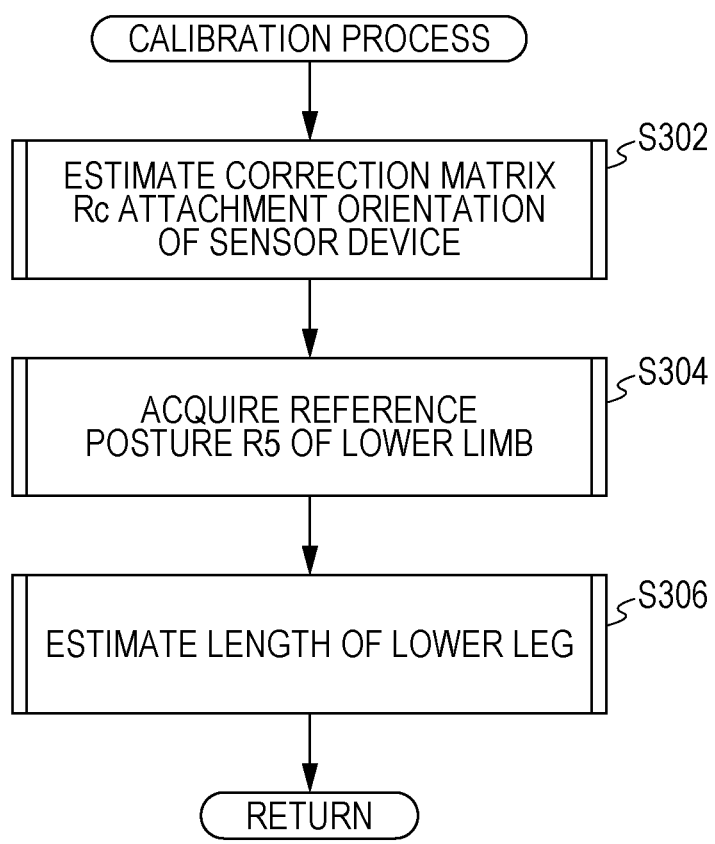
FIG. 5 is a flowchart illustrating an example of a calibration process applied to the exercise information display system according to one embodiment.

FIG. 5 is a flowchart illustrating an example of a calibration process applied to the exercise information display system according to the embodiment.

Figure 6:
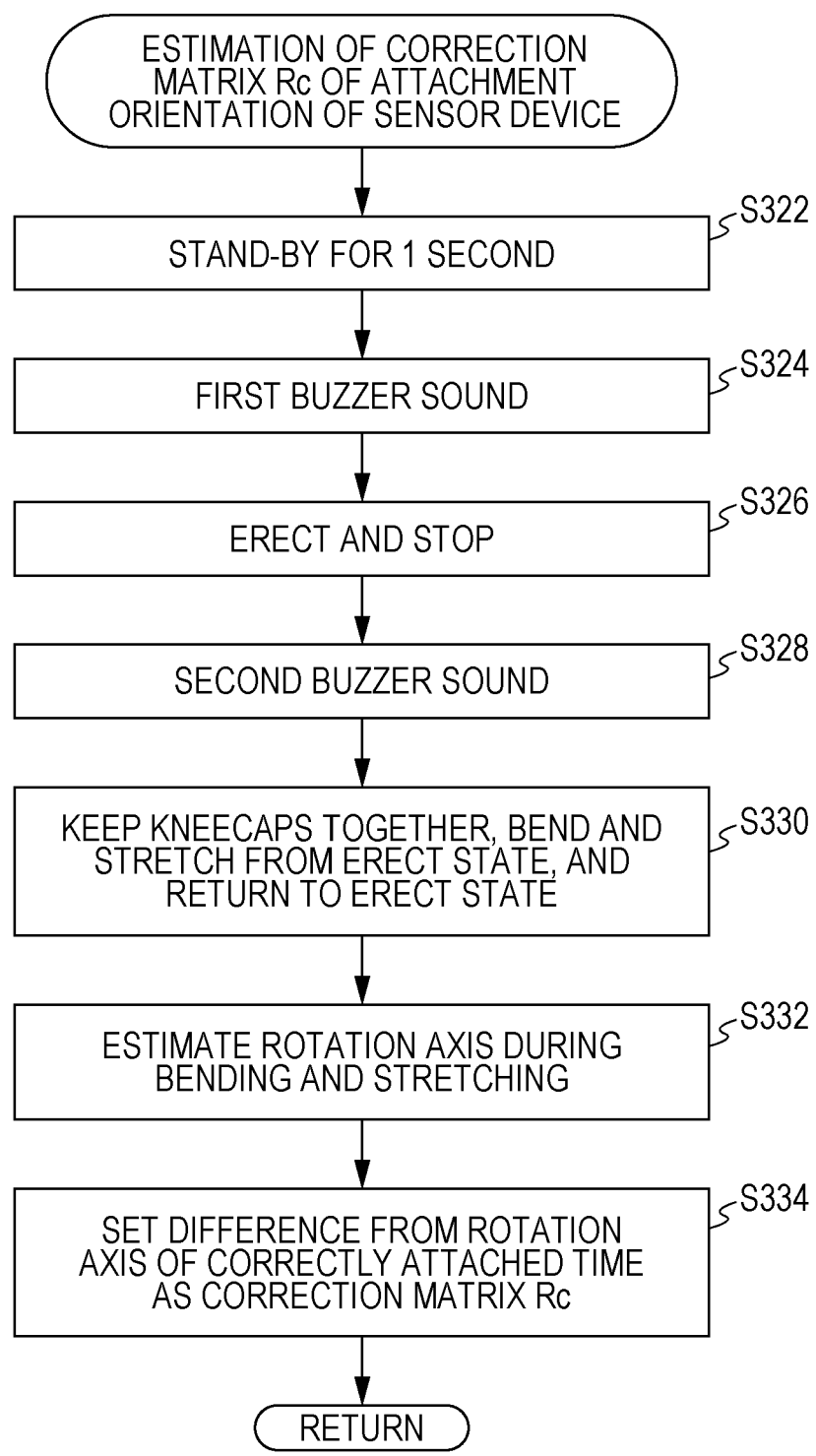
FIG. 6 is a flowchart illustrating an example of an attachment orientation correction matrix estimation process for a sensor device executed in a calibration process applied to one embodiment.

FIG. 6 is a flowchart illustrating an example of an attachment orientation correction matrix estimation process for the sensor device executed in the calibration process applied to the embodiment.

Figure 7:
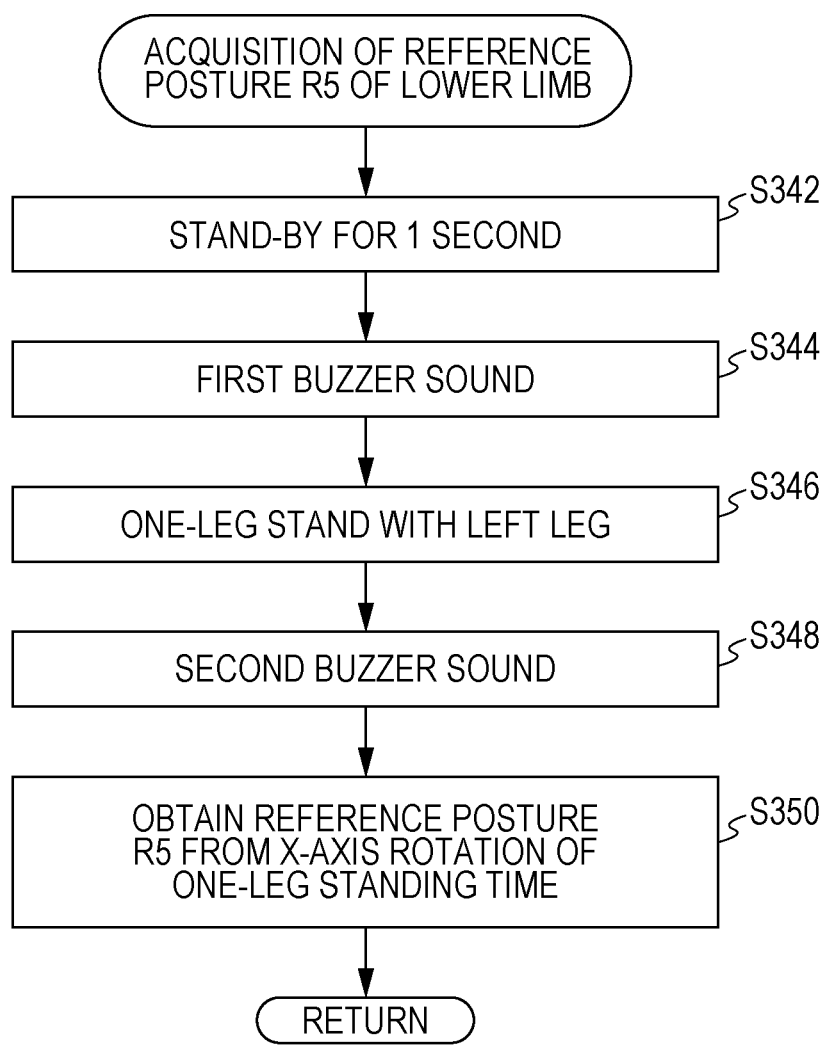
FIG. 7 is a flowchart illustrating an example of a lower limb reference posture setting process executed in the calibration process applied to one embodiment.

FIG. 7 is a flowchart illustrating an example of a lower limb reference posture setting process executed in the calibration process applied to the embodiment.

FIG. 8 is a flowchart illustrating an example of a lower limb length estimation process executed in the calibration process applied to the embodiment.

FIG. 9 is a flowchart illustrating an example of a lower limb length acquisition method (lower limb length acquisition process) executed in the lower limb length estimation process applied to the embodiment.

Figure 10A:
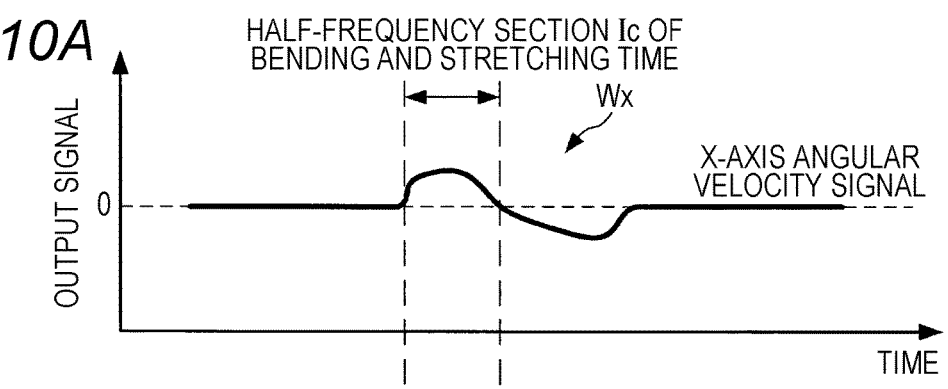
FIGS. 10A, 10B, and 10C are signal waveform diagrams illustrating an example of an output signal of an angular velocity sensor acquired during bending and stretching motion executed in the attachment orientation correction matrix estimation process applied to one embodiment.
Figure 10B:
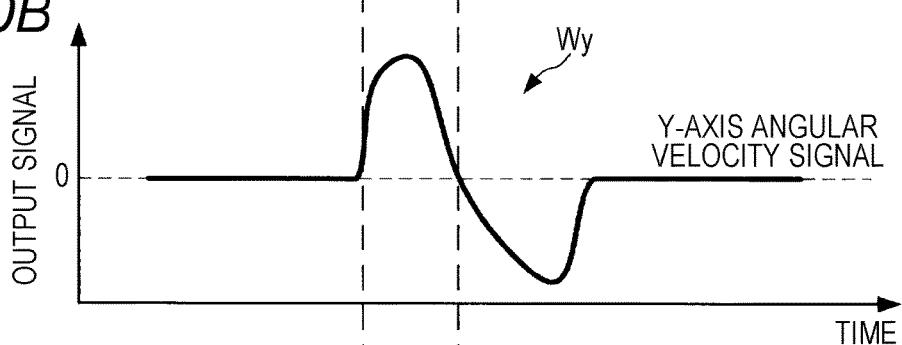
Figure 10C:
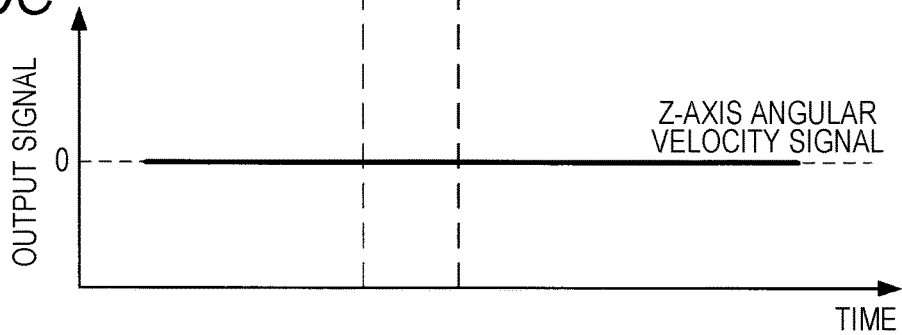

FIGS. 10A, 10B, and 10C are signal waveform diagrams illustrating an example of an output signal of an angular velocity sensor acquired during bending/stretching motion executed in the attachment orientation correction matrix estimation process applied to the embodiment.

Figure 11A:
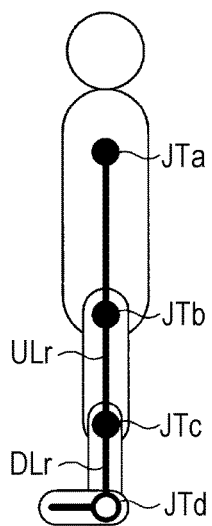
FIGS. 11A, 11B, and 11C are schematic diagrams illustrating an example of a bending motion executed in a lower limb length estimation process applied to one embodiment.
Figure 11B:
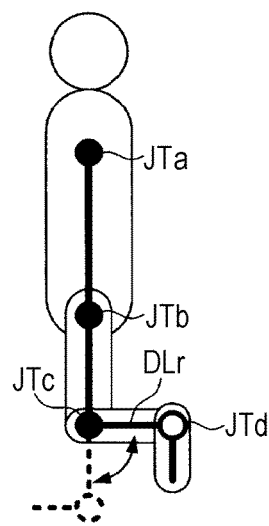
Figure 11C:
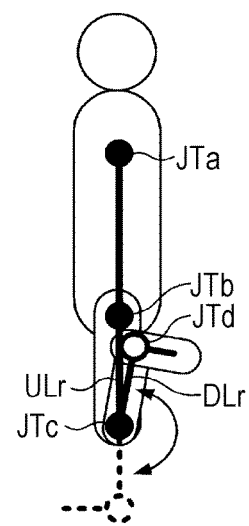

FIGS. 11A, 11B, and 11C are schematic diagrams illustrating an example of bending motion executed in the lower limb length estimation process applied to the embodiment.

In the calibration process applied to the exercise information display system according to the embodiment, as illustrated in the flowchart of FIG. 5, a process regarding application output of the sensor device 100 (attachment orientation correction matrix estimation process; step S302), a process regarding reference posture of a lower limb (lower limb reference posture setting process; step S304) and a process regarding a length of a lower limb (lower limb length estimation process; step S306) are mainly executed.

Herein, a series of the following process operations are realized by executing a predetermined program in the sensor device 100.

In the attachment orientation correction matrix estimation process for the sensor device 100 according to the embodiment, as illustrated in FIG. 6, first, the control unit 140 stands by, for example, for 1 second in the state where the control unit starts a sensing operation in the acceleration sensor 112 and the angular velocity sensor 114 of the sensor unit 110 (step S322), and after that, the control unit controls the notification unit 130 to generate a first buzzer sound having a length of, for example, about 0.5 seconds (step S324).

Next, for example, after 1 second, the control unit 140 controls the notification unit 130 to generate a second buzzer sound having a length of, for example, about 1 second (step S328).

Herein, during the period (for example, 1 second) from the time when the first buzzer sound is generated from the notification unit 130 to the time when the second buzzer sound is generated, the user US maintain a state where the user is erect and unmoving (step S326).

Next, after the second buzzer sound, the user US performs a bending/stretching motion in a state that the user keeps two knees together (in close contact with each other) from the erect state and, after that, performs a motion of returning to the erect state again (step S330).

The control unit 140 executes a correction process for a difference of the attachment orientation of the sensor device 100 to the ankle from correct attachment orientation based on a series of the motions of the user US.

Herein, in the embodiment, the state where the X axis of the sensor coordinate SNC (refer to FIG. 1C) of the sensor device 100 attached to the ankle of the user US is coincident with an advancement direction during the pacing of the user US who is erect, that is, the Z axis of the world coordinate WDC (refer to FIG. 1A) is defined as the correct attachment orientation of the sensor device 100.

On the basis of this, when a real attachment orientation of the sensor device 100 is shifted from the above-described correct attachment orientation, the control unit 140 obtains a matrix (attachment orientation correction matrix) Rc for converting the sensor data output from the sensor unit 110 to sensor data of the case where the sensor device 100 is to be attached with the correct attachment orientation.

Herein, in the state where the attachment orientation of the sensor device 100 is shifted from the correct attachment orientation, when the user US performs the bending/stretching motion in the above-described step S330, signal waveforms output from the angular velocity sensor 114 are illustrated in, for example, FIGS. 10A, 10B, and 10C.

FIG. 10A illustrates a temporal change of an angular velocity signal of the X axis, FIG. 10B illustrates a temporal change of an angular velocity signal of the Y axis, and FIG. 10C illustrates a temporal change of an angular velocity signal of the Z axis.

In FIGS. 10A and 10B, among the characteristic waveform changes Wx and Wy observed in the angular velocity signal waveforms of the X and Y axes, the Wx is caused from that fact that the sensor device 100 is not at the correct attachment orientation with respect to the ankle and the real attachment orientation is shifted in the rotational direction of the Z axis from the correct attachment orientation.

In addition, in the case where the sensor device 100 is attached at the correct orientation with respect to the ankle, the angular velocity signal of the X axis output from the angular velocity sensor 114 is in a substantially constant (flat) state, and the characteristic waveform change Wy is observed from only the angular velocity of the Y axis.

Thus, in the embodiment, as illustrated in FIGS. 10A, 10B, and 10C, the attachment orientation correction matrix Rc for the sensor device 100 is obtained by using a half-period section Ic of the characteristic waveform change Wx observed during the bending/stretching motion of the user US.

First, the control unit 140 estimates a rotation axis of the bending/stretching motion (step S332).

Herein, an average value of the half-period section Ic of the characteristic waveform change Wx observed from the signal waveforms output from the angular velocity sensor 114 is normalized as aveGyr1.

Herein, as the aveGyr1 is viewed as a vector, the aveGyr1 becomes the rotation axis of the bending/stretching motion in the sensor coordinate SNC.

Thus, the control unit 140 obtains the convert matrix (attachment orientation correction matrix) Rc for converting the rotation axis aveGyr1 to the rotation axis vecY [0 1 0] of the case where the sensor device 100 is attached to the correct position by using a series of the following group of equations (step S334).

$vec2 = cross(aveGyr1, vecY)$ $rad1 = a\cos(dot(aveGyr1, vecY))$ $rvec1 = vec2 \times rad1$ Herein, the rvec1 is the rotation vector, and conversion from the rotation vector (axis-angle) to the rotation matrix is the attachment orientation correction matrix Rc.

Herein, cross denotes outer product calculation, dot denotes inner product calculation, and a cos denotes inverse cosine calculation.

The conversion from the rotation vector to the rotation matrix is performed through a quaternion q as follows.

Herein, the quaternion q is a four-element number and is represented by q=[qw, qx, qy, qz].

As expressed in the above equations, since the rotation vector rvec1 is configured with the rotation axis vec2 and the rotation angle rad1, the following relationship is satisfied.

$qw = \cos(0.5 \times rad1)$ $qvec = \sin(0.5 \times rad1)/\mathrm{norm}(vec2)$

Herein, qvec=[qx qy qz], and norm denotes a Euclid norm (a concept of a length) of a vector.

Thus, the attachment orientation correction matrix Rc can be expressed by the following equation (11).

Herein, the attachment orientation correction matrix Rc corresponds to a difference between the rotation axis of the case where the sensor device 100 is attached to be shifted from the correct attachment orientation and the rotation axis of the case where the sensor device 100 is attached with the correct attachment orientation.

[Mathematical Formula 1]

$$Rc = \begin{bmatrix} 1 & 0 & 0 \\ 0 & 1 & 0 \\ 0 & 0 & 1 \end{bmatrix} + \quad (11)$$

$$2 \times \begin{bmatrix} -qy^2 - qz^2 & qx \times qy - qw \times qz & qx \times qz + qw \times qy \\ qx \times qy + qw \times qz & -qx^2 - qz^2 & qy \times qz - qw \times qx \\ qx \times qz - qw \times qy & qy \times qz + qw \times qx & -qx^2 - qy^2 \end{bmatrix}$$

Next, the lower limb reference posture setting process for the user US will be described with reference to the flowchart illustrated in FIG. 7.

In the embodiment, the reference posture denotes a posture used a reference at the time of recovering the motion state of the lower limb of the user US in the lower limb motion reproduction process executed in the information processing device 200 described later.

In the embodiment, a posture of a left leg at the time of one-leg standing with the left leg attached with the sensor device 100 described later is used as the reference posture.

The control unit 140 executes a process of removing a gravitational acceleration component from the acceleration data acquired from the acceleration sensor 112 or a process of setting an absolute posture at the time of integrating the angular velocity data acquired from the angular velocity sensor 114 by using the reference posture.

In addition, a specific method of using the reference posture will be described later in the lower limb motion reproduction process.

In the lower limb reference posture setting process, as illustrated in FIG. 7, first, the control unit 140 stands by, for example, for 1 second in the state where the control unit starts the sensing operation in the acceleration sensor 112 and the angular velocity sensor 114 of the sensor unit 110 (step S342), and after that, the control unit controls the notification unit 130 to generate the first buzzer sound (step S344).

Next, for example, after several seconds, the control unit 140 controls the notification unit 130 to generate the second buzzer sound (step S348).

During the period between the first buzzer sound and the second buzzer sound, the user US performs one-leg stand of taking off the right leg from the ground in the state where the sole of the foot of the left leg attached with the sensor device 100 is in contact with the ground (step S346).

At this time, it is preferable that the lower leg from the knee to the ankle of the left leg be allowed to be as erect as possible. The posture of the left leg at the time of performing the one-leg stand is used as the reference posture.

In the above-described one-leg stand, if the lower leg is in the erect state as viewed from the horizontal direction, that is, the X axis direction of the world coordinate WDC, the acceleration components acquired from the acceleration sensor 112 appear only in the Y axis and the Z axis, but the acceleration component does not appear in the X axis corresponding to the advancement direction.

Thus, in the embodiment, the rotation element of the X axis in the sensor coordinate SNC is extracted from the reference posture. Therefore, the control unit 140 obtains a lower limb reference posture matrix R5 generated from the rotation element of the X axis (step S350).

A rotation angle angle 5 of the X axis in the reference posture is obtained by the following equation.

$angle5 = -a\sin(accy/accz)$

Herein, a sin denotes inverse sine calculation, accy denotes an acceleration component of the Y axis at the time of performing one-leg stand, accz denotes an acceleration component of the Z axis.

These components are the acceleration components of the Y and Z axes of the corrected acceleration data acc obtained by converting the acceleration data acc_in acquired from the acceleration sensor 112 by using the above-described attachment orientation correction matrix Rc as follows.

$acc = Rc \times acc\_\mathrm{in}$

Thus, the lower limb reference posture matrix R5 can be expressed by the following equation (12).

[Mathematical Formula 2]

$$R5 = \begin{bmatrix} 1 & 0 & 0 \\ 0 & \cos(angle5) & -\sin(angle5) \\ 0 & \sin(angle5) & \cos(angle5) \end{bmatrix} \quad (12)$$

In addition, the case of simply one-leg standing with the left leg attached with the sensor device 100 in the above-described lower limb reference posture setting process is described. However, the embodiment is not limited to this method, but the user may perform a motion of jumping, for example, forward or upward, landing with only the left leg attached with the sensor device 100, and stopping at the same time of the landing.

Next, the lower limb length estimation process for the user US will be described with reference to flowcharts illustrated in FIGS. 8 and 9.

In the embodiment, the lower leg length denotes a length from an installation position of the acceleration sensor 112 installed in the sensor device 100 attached in the vicinity of the ankle of the user US to the knee.

In the lower limb length estimation process, as illustrated in FIG. 8, first, the control unit 140 stands by, for example, for 1 second in the state where the control unit starts the sensing operation of the acceleration sensor 112 and the angular velocity sensor 114 in the sensor unit 110 (step S362), and after that, the control unit controls the notification unit 130 to generate the first buzzer sound having a length of, for example, about 0.5 seconds (step S364).

Next, for example, after several seconds, the control unit 140 controls the notification unit 130 to generate the second buzzer sound having a length of, for example, about 1 second (step S368).

During the period between the first buzzer sound and the second buzzer sound, the user US moves (bends the knee) from the state illustrated in FIG. 11A where the lower leg DLr of the left leg attached with the sensor device 100 is erect to the position illustrated FIG. 11B where the position of the knee JTc is not moved as much as possible and the lower leg DLr is rotated 90° backward (the opposite direction of the advancement direction; rightward in the figure) by using the knee JTc as the rotation axis.

After that, as illustrated in FIG. 11A, a series of bending motions of returning the lower leg DLr to the position where the left leg is initially erect are performed (step S366).

In the state illustrated in FIG. 11A, it is preferable that the lower leg DLr is erect to the utmost.

In the bending motion, in order to bend the lower leg DLr by using the knee JTc as an axis, it is preferable that the position of the knee JTc is not moved to the utmost.

In addition, in FIGS. 11A, 11B, and 11C, JTa denotes a chest of the body, JTb denotes a base of the thigh (leg), and JTd denotes an ankle attached with the sensor device 100.

Next, the control unit 140 performs a process of acquiring the lower leg length based on the sensor data acquired at the time when the user US performs a series of the bending motions (period between the first buzzer sound and the second buzzer sound) as follows (step S370).

In the process of acquiring the lower limb length, as illustrated in FIG. 9, first, the control unit 140 the posture matrix R7 for converting the sensor coordinate SNC which is a relative coordinate to the world coordinate WDC1 which is equal to the sensor coordinate SNC in the erect state based on the angular velocity data (step S382).

The world coordinate WDC1 becomes an absolute coordinate used only at the time of acquiring the lower limb length. The X axis of the world coordinate WDC1 is the advancement direction, the Y axis is a left-handed direction of the advancement direction, and the Z axis is a ceiling direction perpendicular to the X axis and the Y axis.

More specifically, the control unit 140 converts the angular velocity data to a rotation vector rvec6 as follows.

$$angle6 = \text{norm}(gyr) \times dt$$

$$vec6 = gyr/\text{norm}(gyr)$$

Herein, the angle 6 is a rotation angle about the rotation axis vec6.

The dt denotes a sampling period (sampling time) of the angular velocity sensor 114 and is set to, for example, 5 msec.

The gyr is a corrected angular velocity data obtained by converting the angular velocity data gyr_in acquired from the angular velocity sensor 114 by using the above-described attachment orientation correction matrix Rc as expressed in the following equation.

$$gyr = Rc \times gyr\_in$$

The rotation vector rvec6 is expressed by the following equation by using the rotation axis vec6 and the rotation angle angle6 described above.

$$rvec6 = vec6 \times angle6$$

Thus, conversion of the rotation vector rvec6 to the rotation matrix by using the method of converting the rotation vector illustrated in the above-described attachment orientation correction matrix (Rc) estimation process to the rotation matrix is the R6.

The rotation matrix used herein is a rotation matrix per time of the sampling period of the angular velocity sensor 114, and since the rotation matrix exists in every sampling motion, the rotation matrix is expressed by R6 {n}. Herein, n denotes a position (that is, frame) of the sampling motion.

Next, by integrating the above-described rotation matrix R6 {n}, the control unit 140 obtains a posture matrix R7 {n} of the position where a change in the reference state appears.

Herein, when the front (initial) posture is used as a reference, the posture matrix R7{n} is calculated by integrating the rotation matrix R6 {n} over all the sampling motions.

For example, the posture matrix R7{3} at the time of the third sampling motion is expressed by the following equation.

$$R7\{3\} = R7\{2\} \times R6\{3\} = R6\{1\} \times R6\{2\} \times R6\{3\}$$

Next, the control unit 140 obtains the value (coordinate-converted acceleration data) acc_w1 of the world coordinate WDC1 by performing coordinate conversion on the acceleration data acc_in acquired from the acceleration sensor 112 by using the above-described posture matrix R7 as expressed by the following equation (step S384).

$$acc\_w1 = R7 \times acc\_in$$

Herein, in the acceleration data acc_in acquired from the acceleration sensor 112 during the real pacing motion, the sensor coordinate SNC is always changed with respect to the world coordinate WDC1 due to the leg motion associated with the pacing motion. Therefore, the direction of the gravitational acceleration is also changed.

On the contrary, as described above, in the coordinate-converted acceleration data acc_w1 obtained by conversion to the world coordinate WDC1 by using the posture matrix R7, the gravitational acceleration is always exerted in the Z axis direction.

Next, the control unit 140 obtains the acceleration data acc configured with only the motion component associated with the motion (herein, a series of the bending motions described above) by removing the gravitational acceleration component from the coordinate-converted acceleration data acc_w1 as expressed by the following equation (step S386).

Herein, the acceleration data acc are values obtained by using the world coordinate WDC1 as a reference.

$$acc = acc\_w1 - [0\ 0\ 9.8]$$

Herein, the unit of the acceleration is m/s².

Next, the control unit 140 converts the acceleration data acc to a position pos through two-times integration of the acceleration data acc of only the motion component (step S388) to obtain the position of the ankle at the time of each sampling motion.

Herein, if a condition that first and final positions in a series of the bending motions by the user US are equal to each other is applied, the lower leg length is calculated as expressed below.

Namely, first, the control unit 140 calculates a velocity vel through one-time integration of the acceleration data acc configured with only the motion component and calculates the position pos through another integration.

$$vel = \Sigma((acc - \text{offset}) \times dt)$$

$$pos = \Sigma(vel \times dt)$$

Herein, dt denotes the sampling period of the angular velocity sensor 114, and offset is expressed by the following equation.

$$\text{offset} = 2 \times \text{position}(N)/(N \times (N+1) \times dt \times dt)$$

Herein, N is the number of samples, and position denotes pos calculated in the case where offset=0 in the velocity vel and the position pos.

Next, the control unit 140 obtains a maximum amount of change in the position pos (world coordinate WDC1) in the Z axis direction and determines the maximum amount of change as a lower leg length leg_len of the user US (step S390).

Herein, in the embodiment, as illustrated in FIGS. 11A and 11B, in a series of the bending motions, since the ankle JTd attached with the sensor device 100 is allowed to be in a circular motion about the knee JTc as an axis, the maximum amount of change in the position space may be determined as the lower leg length leg_len.

In addition, in the embodiment, in the lower limb length estimation process, the case where the knee is fixed as the rotation axis and the bending motion is performed so that the lower leg is rotated by 90 degrees backward is described. However, the present invention is not limited thereto.

Namely, as illustrated in FIG. 11C, the lower leg DLr may be bent by about 180 degrees to the position where the lower leg is in close contact with the thigh ULr.

In the bending motion of this case, by supporting the lower leg with hands, the lower leg DLr may be lifted up to the 180-degree bent position. However, in order to increase calculation accuracy of the lower leg length leg_len, it is preferable that the position of the knee JTc be not moved utmost. A half of the obtained maximum amount of change of the position pos in the Z axis direction is determined as the lower leg length leg_len.

In the above-described bending motion, the lower leg may be bent to an angle range of 90 degrees or more and less than 180 degrees without bending of the lower leg to 180 degrees. In this case, the maximum amount of change of the position pos (world coordinate WDC1) in the X axis direction may be determined as the lower leg length leg_len.

As another method of estimating the lower leg length leg_len, for example, without attaching the sensor device 100 to the ankle, the user US carries the sensor device 100 with the hand and moves the sensor device in the order of ankle position→knee position→ankle position. Similarly to the above-described bending motion, the maximum amount of change of the position pos in this motion may be determined as the lower leg length leg_len.

In this manner, in the embodiment, by executing the above-described calibration process, a parameter (attachment orientation correction matrix Rc) associated with the sensor device 100 and a parameter (reference posture matrix R5, lower leg length leg_len) associated with the body of the user US can be obtained.

The data or information of the parameters obtained by the calibration process is stored in the predetermined storage area of the storage unit 150.

Herein, in the case of acquiring none of these parameters, for example, a preset unit matrix (default value) may be applied as the attachment orientation correction matrix Rc or the reference posture matrix R5.

The lower leg length leg_len may be manually set by the user US, or a default standard value (default value) may be applied.

Namely, preferably, at least one of the above-described parameters is acquired by the above-described calibration process.

In the case where the reference posture matrix R5 in the one-leg stand cannot be acquired, the attachment orientation correction process or the lower leg length estimation process is performed, and the erect posture in two-leg stand may be used as a substitute.

Herein, according to the inventor's test, the calculation accuracy of the reference posture matrix R5 is high in the case of performing the one-leg stand. Therefore, theuse of the erect posture in the two-leg stand as a substitute is preferred only in the case where the reference posture matrix R5 in the one-leg stand cannot be obtained.

In addition, in the embodiment, as a method of leading the user to perform a specific calibration motion (bending/stretching motion, one-leg stand, bending motion) in the above-described calibration process, the method of allowing the notification unit 130 to generate the buzzer sound is described. However, the present invention is not limited thereto.

Namely, if the user can be led to precisely perform a specific motion by a method, the method of generating sound, vibration, and light from various functional unit (sound unit, vibration unit, light emitting unit, and the like) of the notification unit 130 alone or in combination thereof to lead the user may be applied.

In the embodiment, the case where the sensor device 100 as a signal device executes a series of the process operations associated with the above-described calibration process is described. However, the present invention is not limited thereto.

Namely, the sensor data (acceleration data acc_in and angular velocity data gyr_in) acquired from the sensor device 100 may be transmitted to the information processing device 200 through a predetermined communication method, and the information processing device 200 (control unit 240) may execute a series of the process operations associated with the above-described calibration process.

(Lower Limb Motion Reproduction Process)

Next, the lower limb motion reproduction process executed in the control method (exercise information reproducing operation) of the exercise information display system described above will be described in detail with reference to the drawings.

FIG. 12 is a flowchart illustrating an example of a lower limb motion reproduction process applied to the exercise information display system according to one embodiment.

Figure 13:
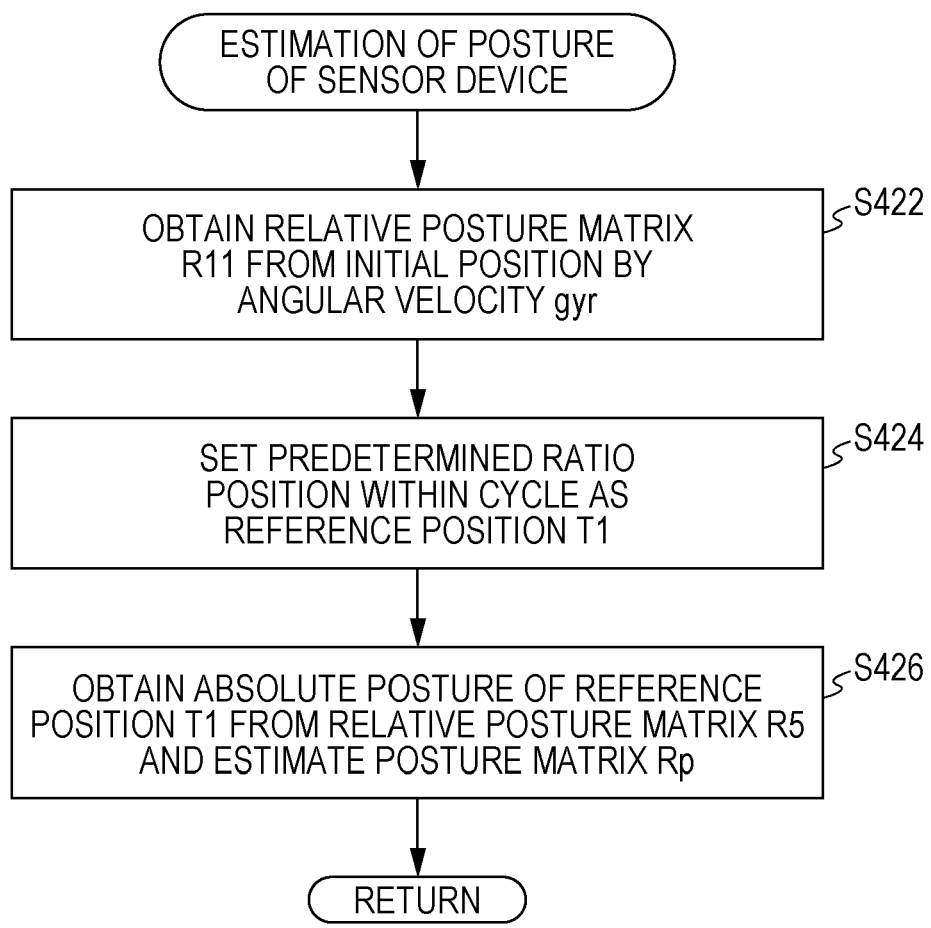
FIG. 13 is a flowchart illustrating an example of a sensor device posture estimation process executed in the lower limb motion reproduction process according to one embodiment.

FIG. 13 is a flowchart illustrating an example of a sensor device posture estimation process executed in the lower limb motion reproduction process applied to one embodiment.

Figure 14:
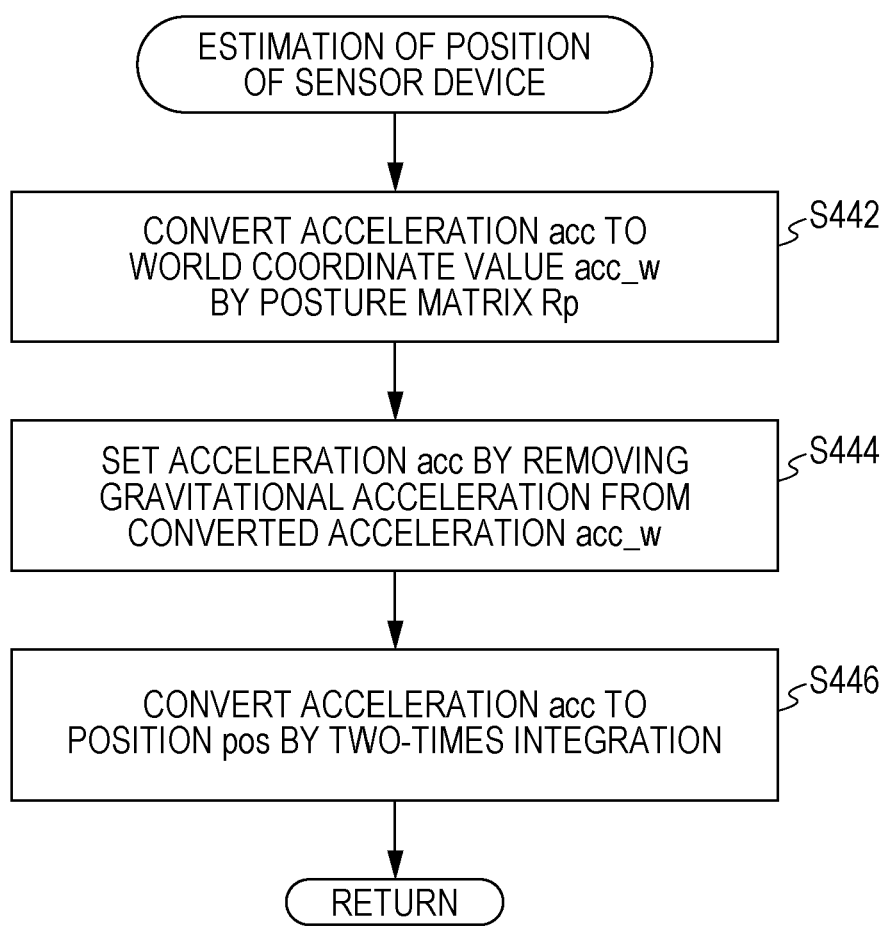
FIG. 14 is a flowchart illustrating an example of a sensor device posture estimation process executed in the lower limb motion reproduction process applied to one embodiment.

FIG. 14 is a flowchart illustrating an example of a sensor device position estimation process executed in the lower limb motion reproduction process applied to one embodiment.

FIG. 15 is a flowchart illustrating an example of a lower limb motion estimation process executed in the lower limb motion reproduction process applied to one embodiment.

FIGS. 16A to 16E are signal waveform diagrams for explaining a cutting-out process for one cycle of running motion in the lower limb motion reproduction process applied to one embodiment.

Figure 17A:
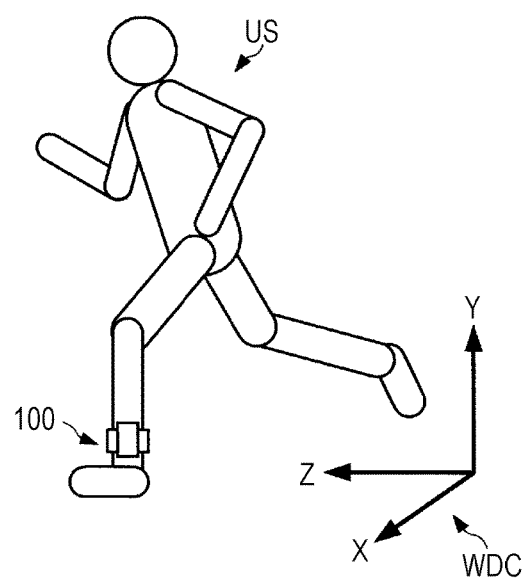
FIGS. 17A and 17B are schematic diagrams illustrating a posture of a user during the cutting-out of one cycle of running motion in the lower limb motion reproduction process applied to one embodiment.
Figure 17B:
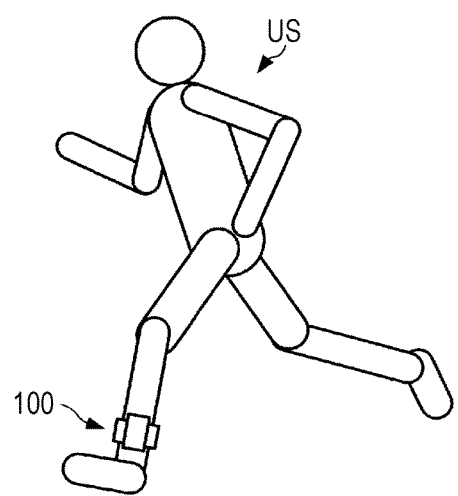

FIGS. 17A and 17B are schematic diagrams illustrating a posture of a user during the cutting out of one cycle of running motion in the lower limb motion reproduction process applied to one embodiment.

FIG. 18 is a schematic diagram illustrating a position of a reference posture of one cycle of running motion in the lower limb motion reproduction process applied to one embodiment.

FIG. 19 is a schematic diagram illustrating an example of a table of a relationship of correspondence between a lower leg length and a motion of a base of a thigh referred to in the lower limb motion reproduction process applied to one embodiment.

Figure 20:
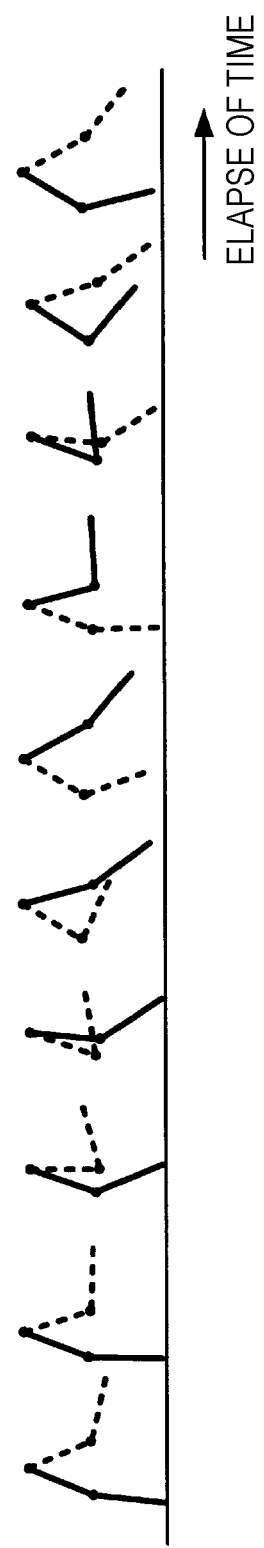
FIG. 20 is a stick model illustrating one cycle of motion of two lower limbs estimated in the lower limb motion reproduction process applied to one embodiment.

FIG. 20 is a stick model illustrating one cycle of a motion of two lower limbs estimated in the lower limb motion reproduction process applied to one embodiment.

The user US sets the sensor device 100 to be in the calibration mode to execute a series of the calibration processes described above, and after that, the user sets the sensor device 100 to be in the measurement mode to do exercise (practice) such as running in the state where the sensor device 100 is attached.

Alternatively, after the above-described calibration process is ended, the sensor device 100 automatically proceeds to the measurement mode.

Therefore, the sensor data including the acceleration data and the angular velocity data are acquired from the acceleration sensor 112 and the angular velocity sensor 114 of the sensor unit 110 to be stored in the predetermined storage area of the storage unit 150 in association with time data.

Next, by the user US setting the sensor device 100 to be in the communication mode, the attachment orientation correction matrix Rc, the reference posture matrix R5, the data or information on the parameters of the lower leg length leg_len, and the sensor data acquired during the exercise which are acquired in the calibration process and stored in the storage unit 150 of the sensor device 100 are transmitted to the information processing device 200 through a predetermined communication method.

The parameters or the sensor data are stored in the predetermined storage area of the storage unit of the information processing device 200 and are used when the information processing device 200 executes the lower limb motion reproduction process.

In the lower limb motion reproduction process applied to the exercise information display system according to the embodiment, as illustrated in the flowchart of FIG. 12, first, the control unit 240 perform a conversion process on the acceleration data acc_in and the angular velocity data gyr_in transmitted from the sensor device 100 by using the attachment orientation correction matrix Rc for the sensor device 100 estimated in the calibration process described above (step S402).

Thus, the corrected acceleration data acc and the corrected angular velocity data gyr are obtained as expressed by the following equations.

$$acc = Rc \times acc\_in$$

$$gyr = Rc \times gyr\_in$$

Figure 16A:
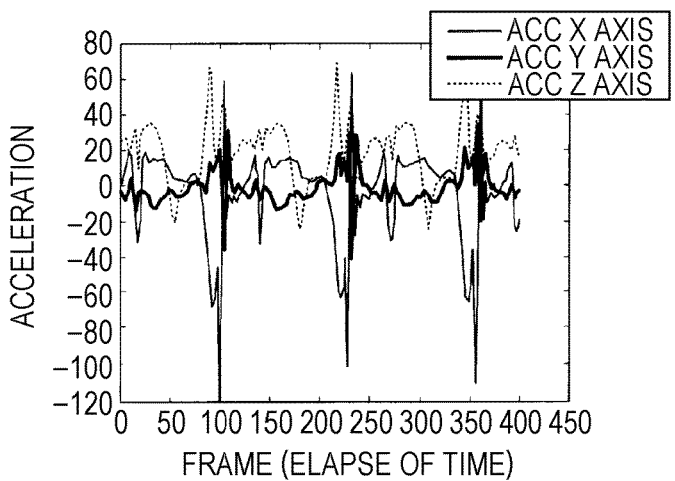
FIGS. 16A, 16B, 16C, 16D, and 16E are signal waveform diagrams for explaining a cutting-out process for one cycle of running motion in the lower limb motion reproduction process according to one embodiment.
Figure 16B:
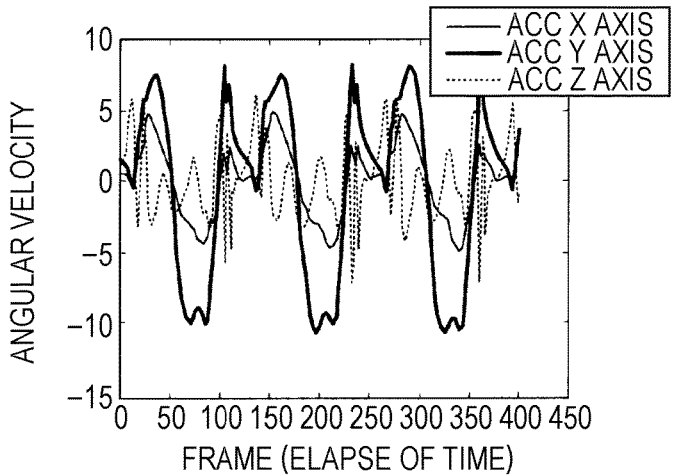

Plural cycles of the signal waveforms of the acceleration data acc and the angular velocity data gyr in the X, Y, and Z axes obtained through the conversion using the attachment orientation correction matrix Rc are illustrated in, for example, FIGS. 16A and 16B.

In the embodiment, in order to prevent error accumulation, the reproduction of the lower limb motion is performed in units of one cycle of the motion (running motion) during the exercise.

Herein, the one cycle of the running motion is a time period from the time when the leg (left leg) attached with the sensor device 100 advances forward through a stroke of the leg motion to the time when the leg advances forward again, that is, a time period of two paces in the running motion.

By repetitively connecting the one cycle of the motion, a continuous motion of the lower limb can be reproduced in a pseudo manner.

Figure 16C:
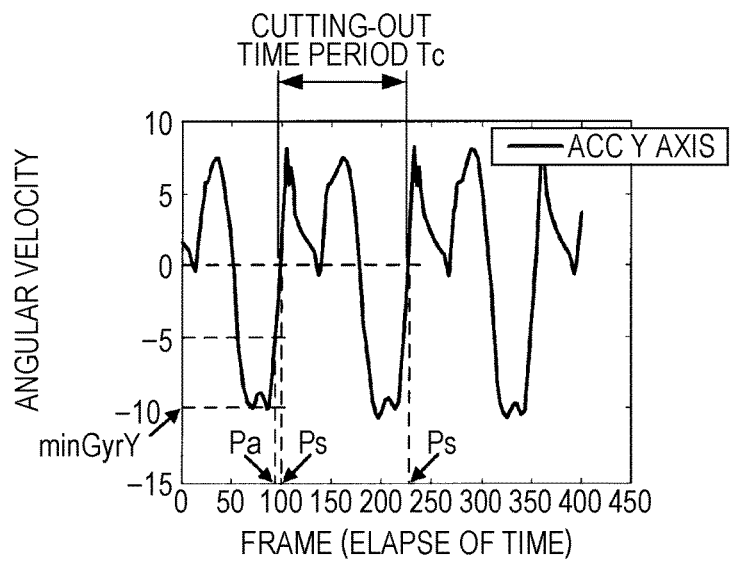

In the embodiment, one cycle of the running motion (cut-out time period Tc) is cut out from the signal form of the angular velocity data gyr illustrated in FIG. 16B, for example, based on the Y-axis component illustrated in FIG. 16C (step S404).

More specifically, first, the control unit 240 considers a time period which is sufficiently longer than the one cycle as a cutting-out object in the signal waveform of the Y-axis component of the angular velocity data gyr illustrated in FIG. 16C, finds a minimum value (minGyrY≈−10) of the angular velocity data gyr, and defines a time position Pa which is a half value thereof (GyrY≈−5) as a start point.

Next, the control unit 240 scans from the time position Pa in the direction of elapse of time (rightward in the figure) and cuts out a time position where the value of the angular velocity data gyr becomes 0 to extract as a position Ps.

For example, as illustrated in FIG. 17B, the exercise posture at the start position Ps is a posture just before the approach to the reference posture (in FIG. 17A, the posture state where the Z axis of the sensor device 100 is coincident with the gravitational axis of the world coordinate WDC) in the above-described calibration process, and the exercise posture at the start position Ps corresponds to the exercise posture in the state where the lower limb attached with the sensor device 100 advances forward.

In the embodiment, the time period between the start position Ps and the next extracted start position Ps in the direction of elapse of time is extracted as one cycle of the cut-out time period Tc.

Next, the signal waveforms of the one cycle of the cut-out time period Tc are cut out in the acceleration data acc and the angular velocity data gyr illustrated in FIGS. 16A and 16B.

Figure 16D:
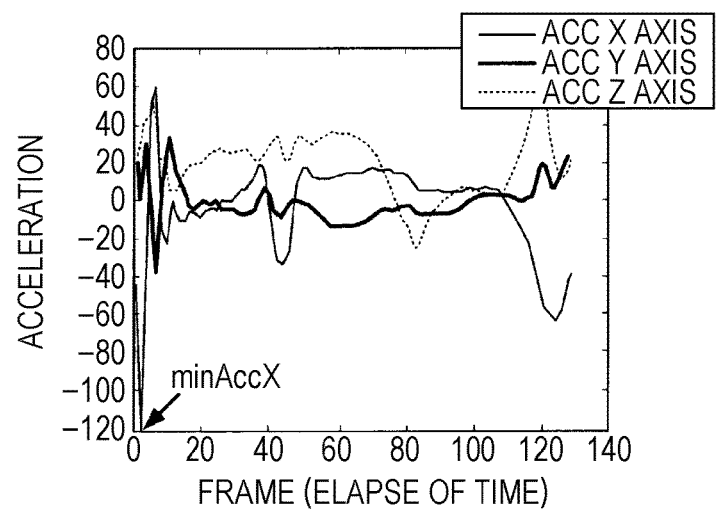
Figure 16E:
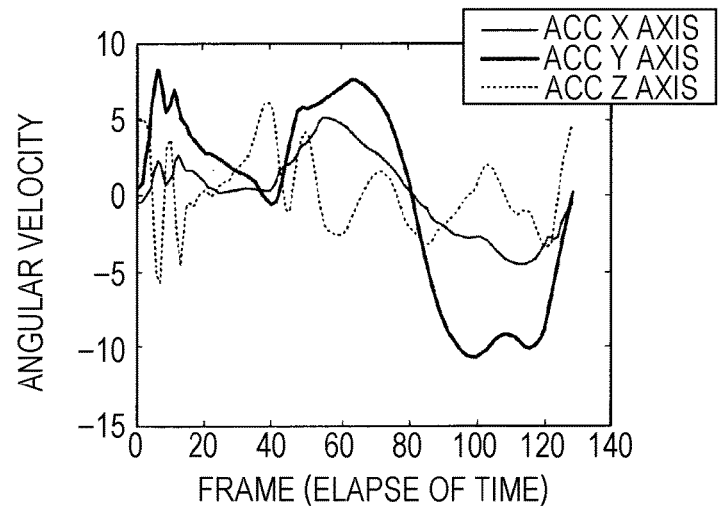

FIGS. 16D and 16E illustrate examples of the one cycle of the signal waveforms cut out from the acceleration data acc and the angular velocity data gyr.

Next, as illustrated in the flowchart of FIG. 12, the control unit 240 sequentially executes a process of estimating the posture of the sensor device 100 based on the angular velocity data gyr (step S406), a process of estimating the position of the sensor device 100 based on the acceleration data acc (step S408), and a process of estimating the lower limb motion based on the motion of the lower leg (step S410).

In the posture estimation process for the sensor device 100, as illustrated in FIG. 13, the control unit 240 obtains the posture matrix Rp with respect to the world coordinate WDC based on the one cycle of the angular velocity data gyr cut out in the cut-out time period Tc.

More specifically, first, the control unit 240 obtains a relative posture matrix R11 on the basis of the initial start position Ps (exposure posture in the state where the leg advances forward) (step S422).

Herein, as a method of obtaining the posture matrix on the basis of the initial posture based on the angular velocity data gyr, the method (refer to step S382) applied in the case of obtaining the posture matrix R7 in the calibration process described above may be applied.

Next, the control unit 240 determines a reference position T1 which is a timing when the lower limb is estimated to have a posture corresponding to the reference posture in the cut-out one cycle (step S424).

Herein, the reference position T1 is a position where the forward advancing leg becomes perpendicular to the ground in the Y-Z plane of the world coordinate WDC and is set to a position when a time period of a predetermined ratio (for example, 7% of one cycle) to the cut-out time period Tc elapses from the start point (that is, the start position Ps) of the cut-out one cycle.

In this case, for example, in the signal waveform of the Y-axis component of the angular velocity data gyr illustrated in FIG. 16C, in the case where the number of frames in one cycle is 143, the 10-th (=143×7%) frame from the start point of the one cycle is set as the reference position T1.

Herein, as the ratio used to define the reference position T1 which is a timing where the posture is estimated to be a posture corresponding to the reference posture, the ratio of the position elapsed from the start point of the one cycle to the cut-out time period Tc is set as follows.

Namely, as illustrated in FIG. 18, if the time of the cut-out one cycle (cut-out time period Tc) is set as 100% and the posture (lower limb motion) of each frame is tested, even in the case where there are individual differences in exercise state (running motion) due to exercise skill, physique, age, gender, or the like, it is verified that the reference posture is almost included in a range of about 3% to 12% of the one cycle. Therefore, the reference position T1 is preferably set to a position with an arbitrary ratio which is in a range of about 3% to 12% of the one cycle.

In the embodiment, it is assumed that, at the reference position T1, the leg of the user US is in the state of the reference posture matrix R5 acquired in the calibration process described above.

Herein, in the case where the above-described ratio used to define the reference position T1 is set to 7%, since the 10-th frame is used as a reference, the posture of the user US at the reference position T1 becomes a coordinate viewed from R5×R11{10} ({ } denotes a function of a frame as a variable).

The control unit 240 obtains the absolute posture of the user US at the reference position T1 by performing coordinate conversion thereof by using the convert matrix cnvR from the sensor coordinate SNC to the world coordinate WDC at the time of further erecting to the wireless communication system.

The control unit 240 estimates the posture matrix Rp based on the absolute posture as expressed by the following equation (step S426).

$$Rp = cnvR \times (R5 \times R11\{10\}) \times R11$$

Herein, the convert matrix cnvR is expressed by the equation (13).

[Mathematical Formula 3]

$$cnvR = \begin{bmatrix} 0 & 1 & 0 \\ 0 & 0 & 1 \\ 1 & 0 & 0 \end{bmatrix} \quad (13)$$

In addition, in the embodiment, the case where the position when the time period of the predetermined ratio (for example, 7%) elapses from the start point of the cut-out one cycle is set as the reference position T1 is described. However, the present invention is not limited thereto.

For example, as illustrated in FIG. 16D, the position where the X-axis component (that is, the acceleration component in the advancement direction of the user US) of the acceleration data acc becomes a negative maximum value (minAccX) from the start point of the cut-out one cycle may be set as the reference position T1.

Next, in the position estimation process for the sensor device 100, as illustrated in FIG. 14, the control unit 240 estimates the position of the sensor device 100 based on the acceleration data acc.

More specifically, first, the control unit 240 obtains the acceleration data acc_w by performing coordinate conversion from the sensor coordinate SNC of the acceleration data acc to the world coordinate WDC by using the posture matrix Rp estimated in the above-described posture estimation process for the sensor device 100 (step S406) as expressed by the following equation (step S442).

$$acc\_w = Rp \times acc$$

Next, since the acceleration data acc_w after the coordinate conversion to the world coordinate WDC include the gravitational acceleration component in the Y axis direction, the control unit 240 obtains the acceleration data acc configured with only the motion component associated with the pacing motion by removing the gravitational acceleration component from the acceleration data acc_w which is converted to the world coordinate WDC by expressed by the following equation (step S444).

$$Acc = acc\_w - [0 \; 9.8 \; 0]$$

Next, the control unit 140 converts the acceleration data acc to the position pos through two-times integration of the acceleration data acc of only the motion component (step S446) to obtain the position of the sensor device 100 at each timing.

Namely, the control unit 140 calculates the velocity Vel through one-time integration of the acceleration data acc configured with only the motion component and calculates the position pos through further integration as expressed by the following equations. In the embodiment, a pacing motion such as running having a periodicity is used.

$$Vel = \Sigma(Acc - aveAcc) \times dt$$

$$Pos = \Sigma(Vel - aveVel) \times dt$$

Herein, aveAcc denotes an acceleration average over one cycle, and aveVel denotes a velocity average.

Next, in the lower limb motion estimation process, as illustrated in FIG. 15, the control unit 240 reproduces in a pseudo manner the lower limb motion based on the position pos of the sensor device 100.

Since the sensor device 100 outputting the sensor data during the pacing motion is attached to the ankle of the user US, the length from the ankle to the knee of the user US is already determined based on the lower leg length leg_len calculated in the above-described calibration process (refer to FIG. 9).

The motion of the position of the ankle of the user US is already estimated based on the above-described position estimation process (refer to FIG. 14) of the sensor device 100.

The posture matrix Rp is also already estimated based on the above-described posture estimation process (refer to FIG. 13) of the sensor device 100.

The orientation from the ankle to the knee of the user US is determined from these data, and the position of the knee is estimated (step S462).

In addition, in general, it is known that the motion of the base of the thigh is much smaller than the motion of the ankle and there are relatively small individual differences.

Thus, in the embodiment, the relationship between the lower leg length and the position of the base of the thigh is predetermined measured, and the relationship is stored in a table format in the storage unit 250.

More specifically, for example, as illustrated in FIG. 19, a table of correspondence of the lower leg length and the position of the base of the thigh over the one cycle is stored as a database in the storage unit 250.

Herein, FIG. 19 is a numeric example (unit: mm), for example, in the case where the one cycle is normalized over 150 frames and the position of the base of the thigh in each frame is indicated by a three-dimensional coordinate (x, y, z).

By referring to the table, the control unit 240 obtains the position of the base of the thigh based on the lower leg length leg_len (step S464).

Thus, the control unit 240 estimates a change in position over the one cycle with respect to three points including the base of the thigh, the knee, and the ankle of the left leg and generates a first reproduction image where the motion state of the left lower limb is reproduced in a pseudo manner.

In addition, with respect to the above-described table, plural types are stored in the storage unit 250 in advance, for example, based on race, gender, age, or the like, and at the time of referring to the table, the user US may specify an extraction condition by using the input manipulation unit 220.

Next, the control unit 240 estimates the change in position of each point of the right leg over the one cycle by delaying (shifting) the position of each point of the left leg by a half period in the time direction and estimates the motion state of the right lower limb to generate a second reproduction image which is to be reproduced in a pseudo manner (step S466).

Next, the control unit 240 combines the first reproduction image and the second reproduction image and connects the bases of the thighs of the two legs with a desired distance (step S468) and estimates the motion state of the two lower limbs over the one cycle as illustrated in FIG. 20 to generate a reproduction image which is to be reproduced in a pseudo manner.

Herein, in FIG. 20, for simplifying the illustration, a stick model (or skeleton model) is used, the left leg attached with the sensor device 100 is indicated by a solid line, and the right leg is indicated by a dotted line. The data of the estimated one cycle of the motion state of the two lower limbs are stored in the predetermined storage area of the storage unit 250.

(Example of Display of Exercise Information)

Next, an example of display of the exercise information applied to the above-described control method for the exercise information display system will be described with reference to the drawings.

Figure 21:
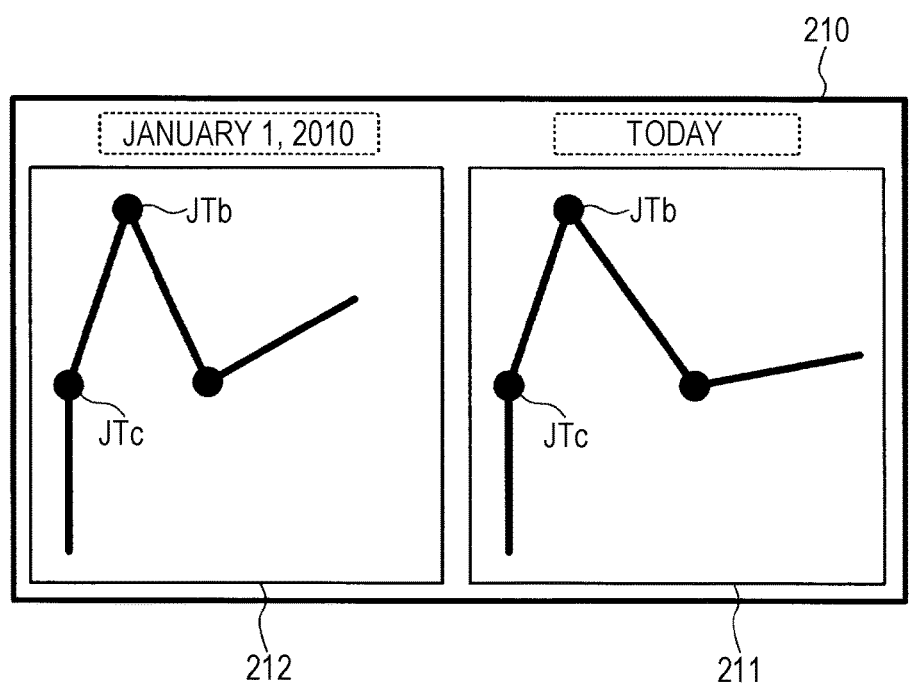
FIG. 21 is a schematic diagram illustrating an example of exercise information displayed in an information processing device applied to the exercise information display system according to one embodiment.

FIG. 21 is a schematic diagram illustrating an example of exercise information displayed in the information processing device applied to the exercise information display system according to the embodiment.

The motion state of the two lower limbs estimated in the above-described lower limb motion reproduction process is displayed in the display unit 210 of the information processing device 200 in a predetermined display format.

More specifically, for example, as illustrated in FIG. 21, the control unit 240 reads data on the currently estimated one cycle of the motion state of the two lower limbs from the storage unit 250 and displays the data in a first display area 211 in a format of an animation (hereinafter, referred to as "stick animation") of the reproduction images using a stick model.

The control unit 240 reads data on the motion state of the lower limb during the previous exercise of the user US as a comparison object in advance in the storage unit 250 and displays the data in a second display area 212 in a format of a stick animation.

In addition, in the storage unit 250, the one cycle of data are is stored so that the posture of the start position during the exercise of the comparative motion state of the lower limb is coincident with that of the currently estimated motion state of the lower limb.

Thus, for example, as illustrated in FIG. 21, the control unit 240 arranges the first display area 211 and the second display area 212 to be adjacent to the screen of the display unit 210 in the horizontal direction (left-right direction in the figure) and performs the display so that the currently estimated motion state of the lower limb and the comparative motion state of the lower limb can be compared.

In addition, the control unit 240 synchronizes the one cycle of the read data with respect to the currently estimated motion state of the lower limb and the one cycle of the read data the comparative motion state of the lower limb and continuously repeats, so that the motion state of the lower limb of the user US and the comparative motion state of the lower limb are displayed according to the stick animation.

In order to facilitate recognition or determination of the motion state of the lower limb, joints such as the base JTb of the thigh and the knee JTc or the like are displayed in the stick animation.

Therefore, the user US can compare and view the currently estimated motion state of the lower limb and the comparative motion state of the lower limb displayed in the display unit 210, and thus, can precisely determine defects, problems, or the like of the motion state (running motion) of the lower limb during the exercise so that the user can reflect the defects, the problems or the like on the subsequent training or the like.

Herein, in FIG. 21, the currently estimated motion state of the lower limb and the comparative motion state of the lower limb are displayed in the stick animations drawn by the same type of lines. However, the present invention is not limited thereto. In order to facilitate the recognition or determination of the motion state of the lower leg, various display forms may be applied or added.

For example, the lower limbs of the left and right legs may be displayed with different colors or difference types of lines, or the motion of the upper body in association with the motion state of the lower limb (lower body) may be added in display.

In addition, the data which the control unit 240 reads from the storage unit 250 as a comparison object and displays in the second display area 212 in a format of the stick animation are not limited to the data during the previous exercise of the user US. For example, data on the motion state of the lower limb of an athlete (elite runner) having higher pacing performance than the user US may be used. In this case, the motion state of the lower limb during the exercise of the user US can be compared with the motion state of the lower limb of the elite runner, and thus, the defects, the problems, or the like of the motion state can be more precisely determined, so that the defects, the problems, or the like can be reflected well on the subsequent training or the like.

In the embodiment, the case where the stick animation where the currently estimated motion state of the lower limb is reproduced in a pseudo manner and the stick animation where the comparative motion state of the lower limb is reproduced in a pseudo manner are arranged in the display unit 210 in the horizontal direction is illustrated. However, the present invention is not limited thereto, but the two stick animations may be displayed to superpose (overlap) each other.

As the information displayed in the display unit 210, in addition to the stick animation of the currently estimated motion state of the lower limb and the stick animation of the comparative motion state of the lower limb, various exercise information based on the sensor data acquired in the measurement mode, for example, numerical values of a maximum kick-up height of the leg, a stride, a pitch (the number of steps per unit time), or the like may be displayed.

In the case where the above-described lower limb motion reproduction process is executed by using a cloud system, the information processing device 200 may be allowed to activate a web browser as software for browsing network information to display exercise information (reproduction image of the lower limb motion or the like) generated as web display data in the cloud system on a web screen of the display unit 210.

In this manner, in the embodiment, by the simple, low-cost configuration where one sensor device including at least the acceleration sensor and the angular velocity sensor is attached to the ankle of the user US, the motion state during the exercise can be precisely determined and can be accurately reproduced, so that the user can reflect the motion state on improvement or the like of training based on the reproduction image in the exercise state.

In particular, in the embodiment, even in the case where the sensor device attached to the ankle of the user is shifted from the normal attachment orientation, without changing the attachment orientation the sensor data acquired during the exercise is corrected by using the attachment orientation correction matrix for the sensor device estimated in the calibration process, so that trouble to correct the attachment orientation of the sensor device is omitted, and the position locus of the sensor device is estimated at a good accuracy, so that the motion of the lower limb of the user can be accurately reproduced.

In the embodiment, even in the case where the lower leg length varies with persons, the lower leg length of the user is estimated in the calibration process, so that the motion of the lower limb of the user can be reproduced with a stick animation based on the position locus of the sensor device at a good accuracy.

In the embodiment, the reference posture of a series of the motion during the exercise of the user is set in the calibration process, and correction of removing the gravitational acceleration component included in the sensor data acquired during the exercise is performed, and thus, the position locus of the sensor device is estimated at a good accuracy, so that the motion of the lower limb of the user can be accurately reproduced.

<Modified Example of Exercise Information Display System>

Next, a modified example of the exercise information display system according to the embodiment will be described.

In the above-described embodiment, the case the sensor device 100 is set to the predetermined operation mode by the user US manipulating the input manipulation unit 120 (manipulation buttons 122 and 124) of the sensor device 100 attached to the ankle is described.

In the modified example of the embodiment, in addition to the sensor device 100, a manipulation device attached to different sites of the body or carried is included, and operation mode setting manipulation for the sensor device 100 or recognition of the operation state thereof is performed through the manipulation device.

FIGS. 22A, 22B, and 22C are schematic configurational diagrams illustrating a modified example of the exercise information display system according to the embodiment. FIG. 22A is a schematic diagram illustrating an example where a sensor device and a manipulation device applied to the modified example are attached to a body, FIG. 22B is a schematic diagram illustrating an outer appearance of the manipulation device, and FIG. 22C is a schematic block diagram illustrating a configurational example of the manipulation device.

Herein, the same components as those of the above-described embodiments (refer to FIGS. 1A, 1B, and 1C and FIGS. 2A and 2B) are denoted by the same or equivalent reference numerals, and the description thereof is simplified.

For example, as illustrated in FIGS. 22A and 22B, an exercise information display system according to the modified example is configured to include a sensor device 100 attached to an ankle of a user US and a manipulation device 300 attached to another site of the body of the user US or carried by the user US to manipulate the sensor device 100.

In addition, although not shown, similarly to the above-described embodiment (refer to FIGS. 1A, 1B, and 1C), the exercise information display system is configured to include an information processing device 200 which reproduces in a pseudo manner an exercise state based on sensor data or the like acquired from the sensor device 100 and provides the exercise state to the user.

As illustrated in FIGS. 22A and 22B, the manipulation device 300 is an electronic device, for example, having a wristwatch-type or wristband-type outer appearance attached to a wrist or the like of the user US.

In addition, in the modified example, as an example of the manipulation device 300, a wristwatch-type or wristband-type electronic device is illustrated. However, the present invention is not limited thereto, but the manipulation device 300 may be, for example, electronic devices having different shapes attached to various sites of the body such as a necklace type attached to the neck, a sport glasses type having an eyeglasses shape, an earphone type attached to the ears, or a mobile device such as a smartphone may be applied.

More specifically, for example, as illustrated in FIG. 22C, the manipulation device 300 is configured mainly to include a display unit 310, an input manipulation unit 320, a notification unit 330, a control unit 340, a storage unit 350, a communication OF unit 360, and a power supply unit 370.

Herein, the manipulation device 300 has at least the functions of the input manipulation unit 120 and the notification unit 130 among the functions of the sensor device 100 illustrated in the above-described embodiment (refer to FIGS. 2A and 2B).

Therefore, the sensor device 100 applied to this modified example may have a configuration where the input manipulation unit 120 and the notification unit 130 are not included.

Namely, the display unit 310 includes a display panel, and the notification unit 330 includes a sound unit, a vibration unit, a light emitting unit, or the like.

The display unit 310 and the notification unit 330 provides or notifies, to the user, at least the information on the procedure in the above-described calibration process, information on operation abnormality of the sensor device 100, or the like through visual perception, auditory perception, tactile perception, and the like. The display unit 310 and the notification unit 330 may provide or notify, to the user, the information or the like on various operations (the calibration process for a predetermined parameter, the sensing operation of the sensor unit 110, transmission operation for the measured sensor date to the information processing device 200, or the like) of the sensor device 100 of which operation mode is set by manipulating the input manipulation unit 320 through visual perception, auditory perception, tactile perception, and the like. Herein, the information provided or notified by the notification unit 330 may be interlocked with the display of the display unit 310.

For example, as illustrated in FIG. 22B, input manipulation unit 320 includes a push button or a slide button installed on a side surface or a front surface of a case of the manipulation device 300, a touch-panel type switch installed on the front surface side (viewing side) of the display unit 310, or the like.

The input manipulation unit 320 is used for manipulation for setting at least an operation mode of the sensor device 100.

The input manipulation unit 320 is also used for manipulation or the like for setting items which are displayed in the display unit 310.

The control unit 140 transmits a control signal to the sensor device 100 through a communication I/F unit 360 described later according to the manipulation of the input manipulation unit 320 and performs controlling of setting the operation mode of the sensor device 100.

The control unit performs controlling of allowing the display unit 310 and the notification unit 330 to provide or notify, to the user, information on various operations such as a calibration process for a predetermined parameter executed in the sensor device 100, a sensing operation of the sensor device 100, transmission operation for the sensor data or the like to the information processing device 200.

The storage unit 350 stores a program for executing the above-described operations or various data or information used or generated when the control unit 140 executes the program.

The communication I/F unit 360 functions as an interface at the time of transmitting the control signal for setting the operation mode of the sensor device 100 or at the time of receiving information on a procedure of the calibration process executed in the sensor device 100.

Herein, as a method of transmitting/receiving signals between the manipulation device 300 and the sensor device 100 through the communication I/F unit 360, for example, various wireless communication methods such as Bluetooth (registered trademark) or Bluetooth low energy (LE) may be applied.

The power supply unit 370 supplies driving power to each component of the manipulation device 300. Similarly to the above-described power supply unit 370 of the sensor device 100, as the power supply unit 370, well-known primary battery or secondary battery, power sources according to energy harvesting technique, or the like may be applied.

In the exercise information display system having the above configuration, besides the functions and effects of the above-described embodiment, the following characteristic functions and effects can be obtained.

Namely, in the modified example, the user US can set the operation mode of the sensor device 100 by manipulating the hand-held manipulation device 300 attached to the wrist or carried with the hand in the state where the sensor device 100 is attached to the ankle.

In the modified example, when the calibration process for a predetermined parameter in the sensor device 100 is executed, the information on the procedure can be provided or notified to the user US through the hand-held manipulation device 300.

Namely, according to the modified example, without bending the body of the user US to directly manipulate the sensor device 100 attached to the ankle, the user US can simply and securely perform a specific motion (erecting motion, bending/stretching motion, or the like) associated with the setting of the operation mode of the sensor device 100 or the calibration process, so that load of the user US can be reduced at the time of using the exercise information display system.

In addition, in the above-described embodiment, as the exercise reproduced in a pseudo manner by the exercise information display system, running is exemplified in the description.

However, the present invention is not limited thereto, but the present invention may be applied to various exercises such as walking, cycling, or swimming Heretofore, while some embodiments of the present invention are described, the present invention is not limited to the embodiment described above, but the invention disclosed in the claims and the equivalence thereof is included.

What is claimed is:
1. An exercise information display system comprising:
a sensor unit which is attached to an ankle of one leg of a human body and outputs data on a motion state of the one leg;
a display unit; and
a control unit which processes the data,
wherein the control unit performs:
acquiring the data as calibration data when the human body performs a calibration motion for acquiring a parameter expressing at least one of an attachment orientation of the sensor unit, an attachment position of the sensor unit on the one leg, and a posture of the one leg when standing on the one leg,
acquiring the parameter based on the calibration data,
acquiring the data as exercise data when the human body performs an exercise of moving at least the one leg, generating a first animation where the motion state of the one leg during the exercise is reproduced in a pseudo manner based on the exercise data and the parameter, estimating a motion state of the other leg during the exercise based on the first animation, and generating a second animation where the motion state of the other leg which is estimated is reproduced in a pseudo manner, generating a reproduction animation where a motion state of the two legs during the exercise is reproduced in a pseudo manner by combining the first animation and the second animation, and displaying at least the reproduction animation as exercise information on the display unit.

2. The exercise information display system according to claim 1, wherein:

the calibration motion includes a first motion where the two legs are bent/stretched in a state where two knees of the two legs are kept together, and the control unit acquires a correction matrix for correcting a difference of the attachment orientation of the sensor unit from a correct attachment orientation as the parameter based on first data output from the sensor unit when the human body performs the first motion as the calibration motion.

3. The exercise information display system according to claim 2, wherein the control unit acquires corrected first data of one cycle of the motion of the human body by converting the first data output from the sensor unit during the exercise by using the correction matrix and generates the reproduction animation based on the corrected first data.

4. The exercise information display system according to claim 1, wherein:

the calibration motion includes a second motion where the one leg is in an erect posture by allowing a sole of a foot of the one leg to be in contact with a ground and the other leg is separated from the ground, and the control unit acquires a posture matrix expressing the reference posture as the parameter based on second data output from the sensor unit when the human body performs the second motion as the calibration motion.

5. The exercise information display system according to claim 4, wherein the control unit estimates a posture of the sensor unit during the exercise in an absolute coordinate by using the posture matrix and generates the reproduction animation based on the estimated posture of the sensor unit.

6. The exercise information display system according to claim 1, wherein:

the calibration motion includes a third motion where the one leg is in an erect posture by allowing a sole of a foot of the one leg to be in contact with a ground, after that, rotating a lower leg of the one leg at least 90 degrees by using a knee of the one leg as a rotation axis, and after that, returning the one leg to an erect posture by allowing the sole of the foot of the one leg to be in contact with the ground, and the control unit acquires a length between the knee of the one leg and the attachment position of the sensor unit as a lower leg length of the one leg as the parameter based on third data output from the sensor unit according to the motion of the human body when the human body performs the third motion as the calibration motion.

7. The exercise information display system according to claim 6, wherein the control unit generates the reproduction animation based on the acquired lower leg length.

8. The exercise information display system according to claim 1, wherein:

the calibration motion includes:

a first motion where the two legs are bent/stretched in a state where two knees of the two legs are kept together;

a second motion where the one leg is in an erect posture by allowing a sole of a foot of the one leg to be in contact with a ground and the other leg is separated from the ground; and a third motion where the one leg is in an erect posture by allowing the sole of the foot of the one leg to be in contact with the ground, after that, rotating a lower leg of the one leg at least 90 degrees by using the knee of the one leg as a rotation axis, and after that, returning the one leg to an erect posture by allowing the sole of the foot of the one leg to be in contact with the ground, and the control unit:

acquires a correction matrix for correcting a difference of the attachment orientation of the sensor unit from a correct attachment orientation as the parameter based on first data output from the sensor unit according to the motion of the human body when the human body performs the first motion as the calibration motion, acquires a posture matrix defining the reference posture based on second data output from the sensor unit according to the motion of the human body when the human body performs the second motion as the calibration motion, acquires a length between the knee of the one leg and the attachment position of the sensor unit as a lower leg length of the one leg as the parameter based on third data output from the sensor unit according to the motion of the human body when the human body performs the third motion as the calibration motion, acquires corrected first data and corrected second data of one cycle of the motion of the human body by converting the first data and the second data by using the correction matrix, estimates a posture of the sensor unit during the exercise in an absolute coordinate by using the posture matrix, estimates a position of the sensor unit during the exercise in the absolute coordinate by removing a gravitational acceleration component from the corrected second data and performing two-times integration, and generates the reproduction animation of the one cycle based on the estimated posture and position of the sensor unit, the acquired lower leg length, and a known relationship between a lower leg length and a position of a base of a thigh of the human body.

9. An exercise information display method comprising:

acquiring data output from a sensor unit as calibration data attached to an ankle of one leg of a human body when the human body performs a calibration motion for acquiring a parameter expressing at least one of an attachment orientation of the sensor unit, an attachment position of the sensor unit on the one leg, and a posture of the one leg when standing on the one leg;

acquiring the parameter based on the calibration data;

acquiring the data as exercise data when the human body performs an exercise of moving at least the one leg;

generating a first animation where the motion state of the one leg during the exercise is reproduced in a pseudo manner based on the exercise data and the parameter;

estimating a motion state of the other leg during the exercise based on the first animation, and generating a second animation where the motion state of the other leg which is estimated is reproduced in a pseudo manner;

generating a reproduction animation where a motion state of the two legs during the exercise is reproduced in a pseudo manner by combining the first animation and the second animation; and displaying at least the reproduction animation as exercise information on a display unit.

10. The exercise information display method according to claim 9, wherein:
the calibration motion includes a first motion where the two legs are bent/stretched in a state where two knees of the two legs are kept together, and
the acquiring the parameter includes acquiring a correction matrix for correcting a difference of the attachment orientation of the sensor unit from a correct attachment orientation as the parameter based on first data output from the sensor unit when the human body performs the first motion as the calibration motion.

11. The exercise information display method according to claim 10, wherein the generating the reproduction animation includes acquiring corrected first data of one cycle of the motion of the human body by converting the first data output from the sensor unit during the exercise by using the correction matrix and generating the reproduction animation based on the corrected first data.

12. The exercise information display method according to claim 9, wherein:
the calibration motion includes a second motion where the one leg is in an erect posture by allowing a sole of a foot of the one leg to be in contact with a ground and the other leg is separated from the ground, and
the acquiring the parameter includes acquiring a posture matrix expressing the reference posture as the parameter based on second data output from the sensor unit when the human body performs the second motion as the calibration motion.

13. The exercise information display method according to claim 12, wherein the generating the reproduction animation includes estimating a posture of the sensor unit during the exercise in an absolute coordinate by using the posture matrix and generating the reproduction animation based on the estimated posture of the sensor unit.

14. The exercise information display method according to claim 9, wherein:
the calibration motion includes a third motion where the one leg is in an erect posture by allowing a sole of a foot of the one leg to be in contact with a ground, after that, rotating a lower leg of the one leg at least 90 degrees by using a knee of the one leg as a rotation axis, and after that, returning the one leg to an erect posture by allowing the sole of the foot of the one leg to be in contact with the ground, and
the acquiring the parameter includes acquiring a length between the knee of the one leg and the attachment position of the sensor unit as a lower leg length of the one leg as the parameter based on third data output from the sensor unit according to the motion of the human body when the human body performs the third motion as the calibration motion.

15. The exercise information display method according to claim 14, wherein the reproduction animation is generated based on the acquired lower leg length.

16. The exercise information display method according to claim 9, wherein:
the calibration motion includes:
a first motion where the two legs are bent/stretched in a state where two knees of the two legs are kept together;
a second motion where the one leg is in an erect reference posture by allowing a sole of a foot of the one leg to be in contact with a ground and the other leg is separated from the ground; and
a third motion where the one leg is in an erect posture by allowing the sole of the foot of the one leg to be in contact with the ground, after that, rotating a lower leg of the one leg at least 90 degrees by using the knee of the one leg as a rotation axis, and after that, returning the one leg to an erect posture by allowing the sole of the foot of the one leg to be in contact with the ground,
the acquiring the parameter includes:
acquiring a correction matrix for correcting a difference of the attachment orientation of the sensor unit from a correct attachment orientation as the parameter based on first data output from the sensor unit according to the motion of the human body when the human body performs the first motion as the calibration motion;
acquiring a posture matrix defining the reference posture based on second data output from the sensor unit according to the motion of the human body when the human body performs the second motion as the calibration motion; and
acquiring a length between the knee of the one leg and the attachment position of the sensor unit as a lower leg length of the one leg as the parameter based on third data output from the sensor unit according to the motion of the human body when the human body performs the third motion as the calibration motion, and
the generating the reproduction animation includes:
acquiring corrected first data and corrected second data of one cycle of the motion of the human body by converting the first data and the second data by using the correction matrix;
estimating a posture of the sensor unit during the exercise in an absolute coordinate by using the posture matrix;
estimating a position of the sensor unit during the exercise in the absolute coordinate by removing a gravitational acceleration component from the corrected second data and performing two-times integration; and
generating the reproduction animation of the one cycle based on the estimated posture and position of the sensor unit, the acquired lower leg length, and a known relationship between a lower leg length and a position of a base of a thigh of the human body.

17. A non-transitory computer-readable recording medium storing an exercise information display program for causing a computer to execute:
acquiring data from a sensor unit as calibration data, the sensor unit being attached to an ankle of one leg of a human body, when the human body performs a calibration motion for acquiring a parameter expressing at least one of an attachment orientation of the sensor unit, an attachment position of the sensor unit on the one leg, and a posture of the one leg when standing one the one leg;

acquiring the parameter based on the calibration data;

acquiring the data as exercise data when the human body performs an exercise of moving at least the one leg;

generating a first animation where the motion state of the one leg during the exercise is reproduced in a pseudo manner based on the exercise data and the parameter;

estimating a motion state of the other leg during the exercise based on the first animation, and generating a second animation where the motion state of the other leg which is estimated is reproduced in a pseudo manner;

generating a reproduction animation where a motion state of the two legs during the exercise is reproduced in a pseudo manner by combining the first animation and the second animation; and displaying at least the reproduction animation as exercise information on a display unit.

* * * * *

UNITED STATES PATENT AND TRADEMARK OFFICE
CERTIFICATE OF CORRECTION

PATENT NO. : 10,105,106 B2
APPLICATION NO. : 14/942803
DATED : October 23, 2018
INVENTOR(S) : Mitsuyasu Nakajima Page 1 of 1

It is certified that error appears in the above-identified patent and that said Letters Patent is hereby corrected as shown below:

In the Claims

Column 33, Line 2, Claim 17, Line 10, delete "one the" and insert --on the--.

Signed and Sealed this
Fifteenth Day of January, 2019

Andrei Iancu
*Director of the United States Patent and Trademark Office*